United States Patent
Eckert et al.

(10) Patent No.: US 10,932,995 B2
(45) Date of Patent: Mar. 2, 2021

(54) DENTAL COMPOSITION WITH HIGH E-MODULUS

(71) Applicant: 3M INNOVATIVE PROPERTIES COMPANY, St. Paul, MN (US)

(72) Inventors: Adrian S. Eckert, Herrsching (DE); Karsten Dede, Landsberg (DE); Christoph H. Thalacker, Weilheim (DE); Gioacchino Raia, Türkenfeld (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/762,170

(22) PCT Filed: Nov. 5, 2018

(86) PCT No.: PCT/IB2018/058675
§ 371 (c)(1),
(2) Date: May 7, 2020

(87) PCT Pub. No.: WO2019/092581
PCT Pub. Date: May 16, 2019

(65) Prior Publication Data
US 2020/0360241 A1    Nov. 19, 2020

(30) Foreign Application Priority Data
Nov. 8, 2017   (EP) .................................. 17200496

(51) Int. Cl.
*A61K 6/891*    (2020.01)
*C07C 69/007*   (2006.01)
*A61C 13/00*    (2006.01)

(52) U.S. Cl.
CPC .......... *A61K 6/891* (2020.01); *A61C 13/0022* (2013.01); *C07C 69/007* (2013.01)

(58) Field of Classification Search
CPC ...... A61K 6/891; A61K 6/00; A61C 13/0022; C07C 69/007
See application file for complete search history.

(56) References Cited

U.S. PATENT DOCUMENTS

| | | |
|---|---|---|
| 3,347,954 A | 10/1967 | Bredereck et al. |
| 3,541,068 A | 11/1970 | Taylor |
| 3,729,313 A | 4/1973 | Smith |
| 3,741,769 A | 6/1973 | Smith |
| 3,808,006 A | 4/1974 | Smith |
| 4,071,424 A | 1/1978 | Dart et al. |
| 4,119,610 A | 10/1978 | Kaelble |
| 4,250,053 A | 2/1981 | Smith |
| 4,259,075 A | 3/1981 | Yamauchi et al. |
| 4,394,403 A | 7/1983 | Smith |
| 4,499,251 A | 2/1985 | Omura et al. |
| 4,537,940 A | 8/1985 | Omura et al. |
| 4,539,382 A | 9/1985 | Omura et al. |
| 4,544,742 A | 10/1985 | Schmitt et al. |
| 4,642,126 A | 2/1987 | Zador et al. |
| 4,652,274 A | 3/1987 | Boettcher et al. |
| 4,772,530 A | 9/1988 | Gottschalk et al. |
| 4,795,823 A | 1/1989 | Schmitt et al. |
| 4,872,936 A | 10/1989 | Engelbrecht |
| 4,874,450 A | 10/1989 | Gottshalk |
| 4,954,414 A | 9/1990 | Adair et al. |
| 5,055,372 A | 10/1991 | Shanklin et al. |
| 5,057,393 A | 10/1991 | Shanklin et al. |
| 5,130,347 A | 7/1992 | Mitra |
| 5,530,038 A | 6/1996 | Yamamoto et al. |
| 5,545,676 A | 8/1996 | Palazzotto et al. |
| 5,624,260 A | 4/1997 | Wilcox et al. |
| 5,865,803 A | 2/1999 | Major |
| 5,893,714 A | 4/1999 | Arnold et al. |
| 5,918,772 A | 7/1999 | Keller et al. |
| 5,944,419 A | 8/1999 | Streiff |
| 6,444,725 B1 | 9/2002 | Trom et al. |
| 6,458,868 B1 | 10/2002 | Okada et al. |
| 6,572,693 B1 | 6/2003 | Wu et al. |
| 6,730,156 B1 | 5/2004 | Windisch et al. |
| 6,769,912 B2 | 8/2004 | Beuschel et al. |
| 6,899,948 B2 | 5/2005 | Zhang et al. |
| 8,329,776 B2 | 12/2012 | Hecht et al. |
| 9,675,529 B2 | 6/2017 | Abuelyman et al. |
| 2003/0008967 A1 | 1/2003 | Hecht et al. |
| 2003/0132539 A1 | 7/2003 | Althoff et al. |
| 2005/0236586 A1 | 10/2005 | Hartung |
| 2006/0187752 A1 | 8/2006 | Keller |

(Continued)

FOREIGN PATENT DOCUMENTS

| | | |
|---|---|---|
| EP | 0 455 854 B1 | 4/1994 |
| EP | 0 712 622 A1 | 5/1996 |
| EP | 1 051 961 A1 | 11/2000 |
| EP | 1 340 472 A1 | 9/2003 |
| GB | 2 181 144 A | 4/1987 |
| WO | WO 2009/151957 A1 | 12/2009 |
| WO | WO 2012/106083 A1 | 8/2012 |

(Continued)

OTHER PUBLICATIONS

Kumar et al., "Bromination of aromatic compounds using ammonium bromide and Oxone®", 2010, *Synthesis*, 10, 1629-32.

*Primary Examiner* — Zohreh A Fay
(74) *Attorney, Agent, or Firm* — 3M IPC

(57) ABSTRACT

The invention relates to a dental composition comprising a resin matrix, a filler matrix in an amount of at least 25 wt. % with respect to the weight of the dental composition, an initiator system, the resin matrix comprising polymerizable monomer(s) comprising two (meth)acrylate moieties connected to a brominated resorcinol, catechol, tyrosol, benzoic acid or phenol moiety. The invention relates also to a dental milling block comprising this composition in its hardened stage.

14 Claims, No Drawings

(56) References Cited

U.S. PATENT DOCUMENTS

| | | |
|---|---|---|
| 2007/0090079 A1 | 4/2007 | Keller |
| 2007/0172789 A1 | 7/2007 | Muller et al. |
| 2008/0187499 A1 | 8/2008 | Wolter et al. |
| 2009/0298966 A1 | 12/2009 | Vanini et al. |
| 2015/0231041 A1 | 8/2015 | Bublewitz et al. |

FOREIGN PATENT DOCUMENTS

| | | |
|---|---|---|
| WO | WO 2015/126862 A1 | 8/2015 |
| WO | WO 2016/142118 A1 | 9/2016 |

DENTAL COMPOSITION WITH HIGH E-MODULUS

CROSS REFERENCE TO RELATED APPLICATIONS

This application is a national stage filing under 35 U.S.C. 371 of PCT/IB2018/058675, filed Nov. 5, 2018, which claims the benefit of European Application No. 17200496.2, filed Nov. 8, 2017, the disclosures of each of which are incorporated by reference herein in their entireties.

FIELD OF THE INVENTION

The invention relates to a dental composition having a high E-modulus which is in particular useful for restorative purposes and for producing dental milling blocks.

The composition comprises a resin matrix comprising polymerizable monomer(s) comprising two (meth)acrylate moieties connected to a brominated resorcinol, catechol, tyrosol, benzoic acid, or phenol moiety, a filler matrix and an initiator system and shows good physical properties.

BACKGROUND

Dental restorative materials are typically composed of a resin matrix and a filler matrix and need to fulfil a couple of different properties.

Besides the requirement of being non-toxic, they have to be sufficiently stiff and hard enabling them to withstand chewing forces over many years and ideally also be aesthetically acceptable.

Thus, the material the dental restorations are made of should meet a balance between hardness and elasticity.

One physical parameter which is sometimes used for determining the stiffness is the elastic modulus (E-modulus).

The E-modulus of a dental restoration or restorative material is typically influenced by the monomers used for the resin matrix and the amount of filler contained in the composition. There are various attempts to improve the E-modulus of dental restorative materials.

US 2015/0231041 A1 (Bublewitz et al.) describes polymerizable dental materials containing a) at least one curable aliphatic and/or cycloaliphatic monomer system containing one aliphatic and/or cycloaliphatic bis(meth)acrylate and/or an aliphatic and/or cycloaliphatic bis(meth)acrylamide and b) a certain filler. Compositions with an E-modulus in the range of 7-8 GPa are reported.

WO 2016/142118 A1 (Ivoclar Vivadent) describes dental materials based on hybrid monomers which are said to have excellent mechanical properties after curing. Compositions with an E-modulus in the range of 6-8 GPa are reported.

US 2008/0187499 A1 (Wolter et al.) relates to a dental composite containing a matrix comprising a silicic acid polycondensate with a —O—CO—NH— moiety and a nano-particulate filler. Compositions with an E-modulus in the range of 8 to 11 GPa are reported.

WO 2012/106083 A1 (3M) relates to a dental composition comprising a certain compound (A), a filler (B), and an initiator (C), wherein compound (A) comprises a certain backbone unit and one or two spacer units having a certain structure.

WO 2015/126862 A1 (3M) describes a dental composition comprising a polymerizable monomer (1), initiator component(s), filler component (2) in an amount of more than about 20 wt. %, wherein monomer (1) is characterized by having two (meth)acrylate reactive moieties, having an unsymmetrical backbone as linkage between the (meth)acrylate reactive moieties, the two (meth)acrylate reactive moieties being attached onto the unsymmetrical monomer backbone as alkyl esters, the unsymmetrical backbone comprising one aromatic moiety of the phenolic type, the polymerizable monomer (1) not containing an acidic moiety, other atoms than carbon, hydrogen, and oxygen, bisphenol moieties.

U.S. Pat. No. 9,675,529 B2 (Abuelyman et al.) relates to a curable dental composition comprising at least one dental resin comprising at least two ethylenically unsaturated groups, a high refractive index monomer, an addition fragmentation agent and optionally an inorganic oxide filler.

SUMMARY OF INVENTION

There is still a need for a curable dental composition with suitable or improved mechanical or physical properties. In particular, there is a need for a dental composition with a sufficiently high E-modulus. The dental composition should also be storage stable.

Ideally, the dental composition has a sufficiently high E-modulus is storage stable and can be polymerized under ambient conditions.

The curable dental composition should be useful as dental restorative material and for producing a dental mill blank.

At least one of these objects is addressed by the present invention.

In one embodiment the invention features a dental composition comprising
- a resin matrix,
- a filler matrix in an amount of at least 25 wt. % with respect to the weight of the dental composition,
- an initiator system,
- the resin matrix comprising polymerizable monomer(s) with two polymerizable moieties connected to a brominated resorcinol, catechol, tyrosol, benzoic acid or phenol moiety and mixtures of these monomers.

In particular, the brominated polymerizable monomer(s) according to formula (I) were found to be useful:

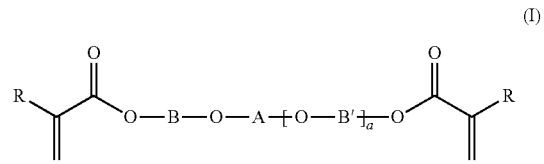

(I)

with:
B—O-A-[—O—B'-]$_a$ representing the monomer backbone as linkage between the reactive (meth)acrylate moieties,
a=0 or 1,
A being selected from:

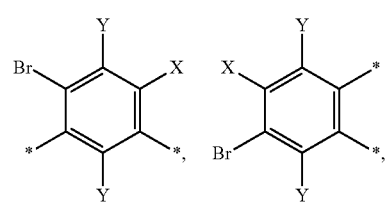

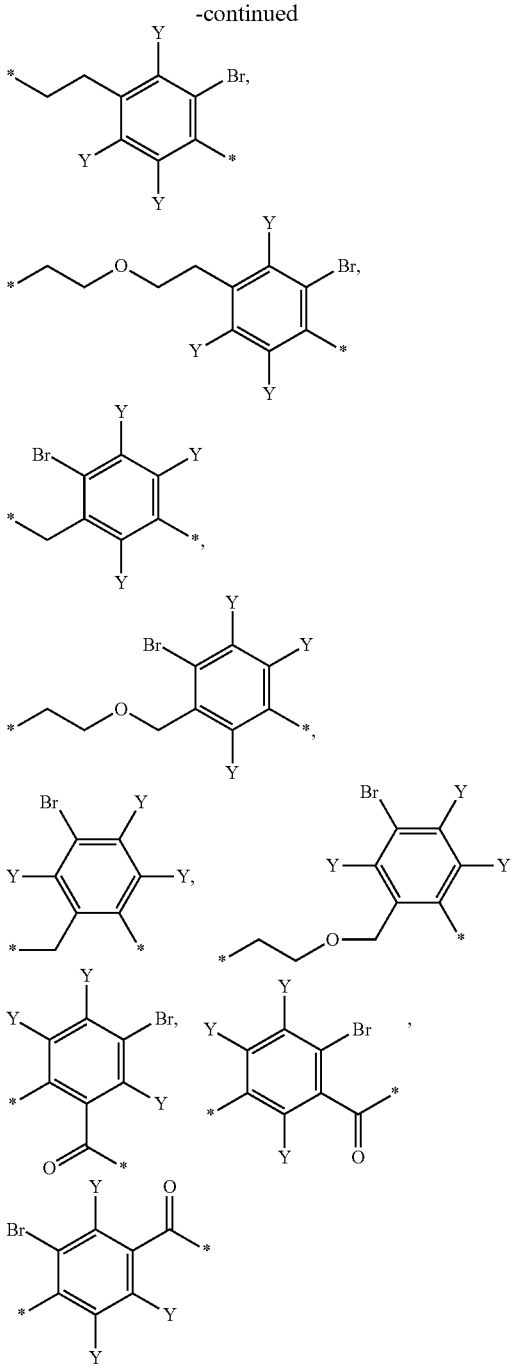

A being always attached as aryl-alkyl ether onto B and/or B',
B being selected from:
*—(CH$_2$)$_b$—*,  *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*,

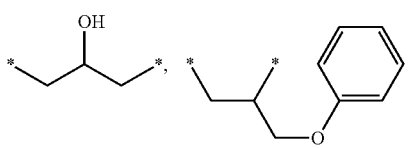

B being always attached as alkyl ester onto the (meth)acrylate reactive moiety, b=2 to 6,
B' being selected from *—(CH$_2$)$_{b'}$—*, *—(CH$_2$—CH$_2$—O—CH$_2$—CH$_2$)—*,

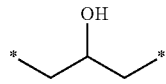

B' being always attached as alkyl ester onto the (meth)acrylate reactive moiety, b'=2 to 6,
R=H, methyl,
X being selected from H, methyl, ethyl, hexyl, tert-butyl, Br, Y=H, Br,
"*" representing those site(s) of a moiety of the monomer, where that moiety is bonded to another moiety of the monomer, as described in the present text and the claims.

In another embodiment, the invention relates to the dental composition for use as a dental restorative material as described in the present text and the claims.

A further embodiment of the invention is directed to dental milling block comprising the dental composition as described in the present text and the claims.

Unless defined differently, for this description the following terms shall have the given meaning:

The term "compound" or "component" is a chemical substance which has a particular molecular identity or is made of a mixture of such substances, e.g., polymeric substances.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A "dental composition" or a "composition for dental use" or a "composition to be used in the dental field" is any composition which can and is to be used in the dental field. In this respect the composition should not be detrimental to the patients' health and thus free of hazardous and toxic components being able to migrate out of the composition. Examples of dental compositions include permanent and temporary crown and bridge materials, artificial crowns, anterior or posterior filling materials, dental mill blanks and orthodontic devices.

Dental compositions are typically hardenable compositions. Dental compositions for hardening in the mouth can be hardened at ambient conditions, including a temperature range of 15 to 50° C. or 20 to 40° C. within a time frame of 30 min or 20 min or 10 min. Higher temperatures are not recommended as they might cause pain to the patient and may be detrimental to the patient's health. Dental compositions are typically provided to the practitioner in comparable small volumes, that is volumes in the range of 0.1 to 100 ml or 0.5 to 50 ml or 1 to 30 ml. Thus, the storage volume of useful packaging devices is typically within these ranges.

A "dental filling material" is a hardenable material designed to restore missing tooth structure, in particular to fill a cavity in hard dental tissue.

A "crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month). A long-term crown and bridge material is typically used over a time period of about 6 to 24 months.

By "dental milling block" or "dental mill blank" is meant a solid block (3-dim article) of material from which a dental article can be machined. A dental milling block has typically a geometrically defined shape. A dental milling block may have a size of 20 mm to 30 mm in two dimensions, for example may have a diameter in that range, and may be of a certain length in a third dimension. A block or blank for making a single crown may have a length of 15 mm to 30 mm, and a block or blank for making bridges may have a length of 40 mm to 80 mm. A typical size of a block or blank as it is used for making a single crown has a diameter of about 24 mm and a length of about 19 mm. Further, a typical size of a block or blank as it is used for making bridges has a diameter of about 24 mm and a length of about 58 mm. Besides the above mentioned dimensions, a dental milling block may also have the shape of a cube, a cylinder or a cuboid. Larger milling blocks may be advantageous if more than one crown or bridge should be manufactured out of one blank. For these cases, the diameter or length of a cylindric or cuboid shaped mill blank may be in a range of 80 to 200 mm, with a thickness being in the range of 10 to 30 mm.

By "machining" is meant milling, grinding, cutting, carving, or shaping a material by a machine. Milling is usually faster and more cost effective than grinding.

An "initiator system" or "initiator" includes those components of the dental composition being able to start or initiate the curing process of the hardenable components, also described herein as "curing the hardenable components".

A "resin matrix" means the organic part of the dental composition being composed of the hardenable components and organic diluents, if present.

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. Typical examples of polymerizable groups include unsaturated carbon groups, such as a vinyl group being present e.g. in a (meth)acrylate group.

A "curable composition" is a mixture of two or more components, the mixture being able to be cured or solidified e.g., by heating to cause chemical crosslinking, radiation-induced polymerization or crosslinking by using a redox initiator. A curable composition may advantageously include a hardenable component.

A "monomer" is any chemical substance which can be characterized by a chemical formula, bearing one or more polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2$=CH—C(O)—O—) and/or a methacryloxy group (i. e., $CH_2$=C($CH_3$)—C(O)—O—). Similarly, (meth)acrylate is a shorthand term referring to "acrylate" and/or "methacrylate." A "urethane group" is a group having the structure "—NH—CO—O—". A "component having a resorcinol moiety" means a component comprising a benzene-1,3-dioyl structural unit.

A "component having a catechol moiety" means a component comprising a benzene-1,2-dioyl structural unit.

A "component having a tyrosol moiety" means a component comprising a 4-(ethylene-1,2-diyl)phenoxy structural unit.

A "solvent" means a liquid which is able to at least partially disperse or dissolve a component at ambient conditions (e.g. 23° C.). A solvent typically has a viscosity below 5 or below 1 or below 0.1 Pa*s.

"Curing," "hardening," and "setting reaction" are used interchangeably and refer to a reaction, wherein physical properties such as viscosity and hardness of a composition change (e.g., increase) over time due to a chemical reaction between the individual components.

A "polymerizable monomer(s) with acidic moieties" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3$H or sulfinic acid residues such as —$SO_2$H.

A "phenolic type" moiety is generally understood as an aromatic moiety bearing at least one oxygen atom directly attached onto an aromatic residue, more precisely, a moiety comprising the structural element [$C_6R_xO$] with x being 1, 2, 3, 4, 5 or 6, R being H, alkyl (e.g. $C_1$ to $C_8$), —O—, —CO— or —C(O)O— and $C_6$ forming an aromatic ring. For example, "$C_6H_5O$—" (phenoxy) represents the most simple "phenolic type" moiety.

A "powder" means a dry, bulk solid composed of a large number of very fine particles that may, for example, flow freely when shaken or tilted.

A "particle" means a substance being a solid having a shape which can be geometrically determined. Particles can typically be analysed with respect to e.g. particle size or diameter. Particles may be amorphous or crystalline.

The term "associated" refers to a grouping of two or more primary particles that are aggregated and/or agglomerated.

Similarly, the term "non-associated" refers to two or more primary particles that are free or substantially free from aggregation and/or agglomeration.

"Aggregated," as used herein, is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972).

Further breakdown of the aggregates into smaller entities may occur during a polishing step applied to the surface of a composition containing the aggregated filler but not during dispersing the aggregated particles in a resin.

Aggregated fillers and processes for the production and surface treatment thereof are described e.g. in U.S. Pat. No.

6,730,156 (Windisch et al.). The content of these references is herewith incorporated by reference.

"Agglomerated" is descriptive of a weak association of particles usually held together by charge or polarity and can be broken down into smaller entities.

Agglomerated fillers are commercially available e.g. from Degussa, Cabot Corp or Wacker under the product designation Aerosil™, CAB-O-SIL™ and HDK.

A "non-agglomerated filler" means that the filler particles are present in the resin in a discrete, un-associated (i.e. non-agglomerated and non-aggregated) stage. If desired this can be proven by TEM microscopy.

Non-agglomerated nano-sized silicas are commercially available e.g. from Nalco Chemical Co. (Naperville, Ill.) under the product designation NALCO™ COLLOIDAL SILICAS e.g. NALCO products 1040, 1042, 1050, 1060, 2327 and 2329.

Non-agglomerated fillers are used and described e.g. in EP 2 167 013 B1 (3M). The content of this reference is herewith incorporated by reference.

The term "primary particle size" refers to the size of a non-associated single crystal zirconia particle, which is considered to be a primary particle. X-ray diffraction (XRD) is typically used to measure the primary particle size.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A "nano-filler" is a filler, the individual particles thereof have a size in the region of nanometers, e.g. an average particle diameter of less than about 200 nm or less than about 100 nm or less than about 50 nm. Useful examples are given in U.S. Pat. No. 6,899,948/Zhang et al.) and U.S. Pat. No. 6,572,693 (Wu et al.). The content with regard to nano-sized silica particles is herein incorporated by reference.

The measurement of the size of nano-particles is preferably based on a TEM (transmission electron microscopy) method, whereby a population is analyzed to obtain an average particle diameter. A preferred method for measuring the particle diameter can be described as follows:

Samples with a thickness not exceeding 80 nm are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

"Radiation curable" shall mean that the component (or composition, as the case may be) can be cured by applying radiation, preferably electromagnetic radiation with a wavelength in the visible light spectrum under ambient conditions and within a reasonable time frame (e.g. within 15, 10 or 5 min).

The term "visible light" is used to refer to light having a wavelength of 400 to 700 nanometers (nm). "Hard dental tissue" means dentin and enamel.

"Additive manufacturing" means processes used to make 3-dimensional articles. An example of an additive manufacturing technique is stereolithography (SLA) in which successive layers of material are laid down under computer control and are subsequently cured by radiation. The articles can be of almost any shape or geometry and are produced from a 3-dimensional model or other electronic data source.

Other examples of additive manufacturing processes or techniques include 3d-printing.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory ambient conditions are typically adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The terms "comprise" or "contain" and variations thereof do not have a limiting meaning where these terms appear in the description and claims. The term "comprise" shall include also the terms "consist essentially of" and "consist of".

"And/or" means one or both. E.g., the expression component A and/or component B refers to a component A alone, component B alone, or to both component A and component B.

DETAILED DESCRIPTION

The dental composition described in the present text and the claims has a couple of advantageous properties.

A hardened dental composition comprising the brominated polymerizable monomers described in the present text shows good physical properties.

The brominated polymerizable monomers described in the present text typically do not solidify at room temperature and have a low viscosity.

This may facilitate the incorporation of a sufficiently high amount of filler, an amount suitable for formulating or producing a dental filling material, a crown and bridge material or a dental mill block.

Surprisingly it was found, that by using brominated polymerizable monomers instead of non-brominated monomers, the E-modulus of the respective dental composition can be improved.

The brominated polymerizable monomers of the present text also typically have refractive index which matches with the refractive index of fillers which are typically used in the dental area.

This allows the formulation of an aesthetically acceptable dental composition, e.g. a dental composition having a suitable transparency. This property may also contribute to a sufficient depth of cure of the curable composition.

In addition, due to the presence of bromine atoms in the polymerizable monomers, the x-ray visibility of the respective dental composition can be improved.

Thus, the invention allows the formulation of a dental composition with advantageous mechanical properties without using bisphenol moiety(s) containing monomers.

In certain embodiments, the dental composition described in the present text can be characterized by the following features (before hardening) alone or in combination:
 a) viscosity: being a paste, e.g. having a viscosity of 5 to 200 Pa*s or 10 to 100 Pa*s measured at 23° C. with a shear rate of 100 l/s;
 b) pH value, if brought in contact with water: 2 to 8, neutral (e.g. 6 to 8) or acidic (e.g. 2 to 5);
 c) radiation and/or redox curable;
 d) being storage stable for at least 3 months;
 e) being provided as a one or two-component system.

A combination of the following properties is sometimes preferred: a), b) and c); a), b), c) and d).

If desired, the viscosity can be determined under the following conditions: 23° C.; shear rate: 100 l/s; measured with a cone/plate geometry CP25-1 with a Physica MCR 301 Rheometer, Anton Paar GmbH, Graz, Austria.

If dissolved or dispersed in water (e.g. 1 g composition in 10 ml water) the dental composition typically exhibits a pH value in the range of 6 to 8 or about 7. That is, the dental composition as a whole essentially has a neutral pH, if brought in contact with water, or is slightly acidic.

The dental composition described in the present text can be hardened in an acceptable time frame, e.g., within less than 300, 180 or 120 s. This can be done by using visible light source equipment already available in the dental office.

In certain embodiments the dental composition (after hardening) fulfils the following properties alone or in combination:
 a) flexural strength: at least 100 or from 100 to 180 MPa according to ISO 4049:2009(E);
 b) E-modulus: at least 10, 11 or 12 or from 10 to 20 or from 11 to 15 determined according to ISO 4049:2009 (E).

The dental composition described in the present text comprises a resin matrix.

The resin matrix comprises brominated polymerizable monomer(s) which contain an aromatic moiety being different from bisphenol, in particular a brominated resorcinol, catechol, tyrosol, benzoic acid, or phenol moiety.

The polymerizable monomer(s) can comprise symmetric or non-symmetric monomers or a mixture thereof.

The polymerizable monomers can be described by the following formula (I):

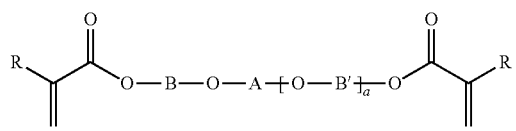

(I)

with:
 B—O-A-[—O—B'-]$_a$ representing the monomer backbone as linkage between the reactive (meth)acrylate moieties,
 a=0 or 1, A being selected from:

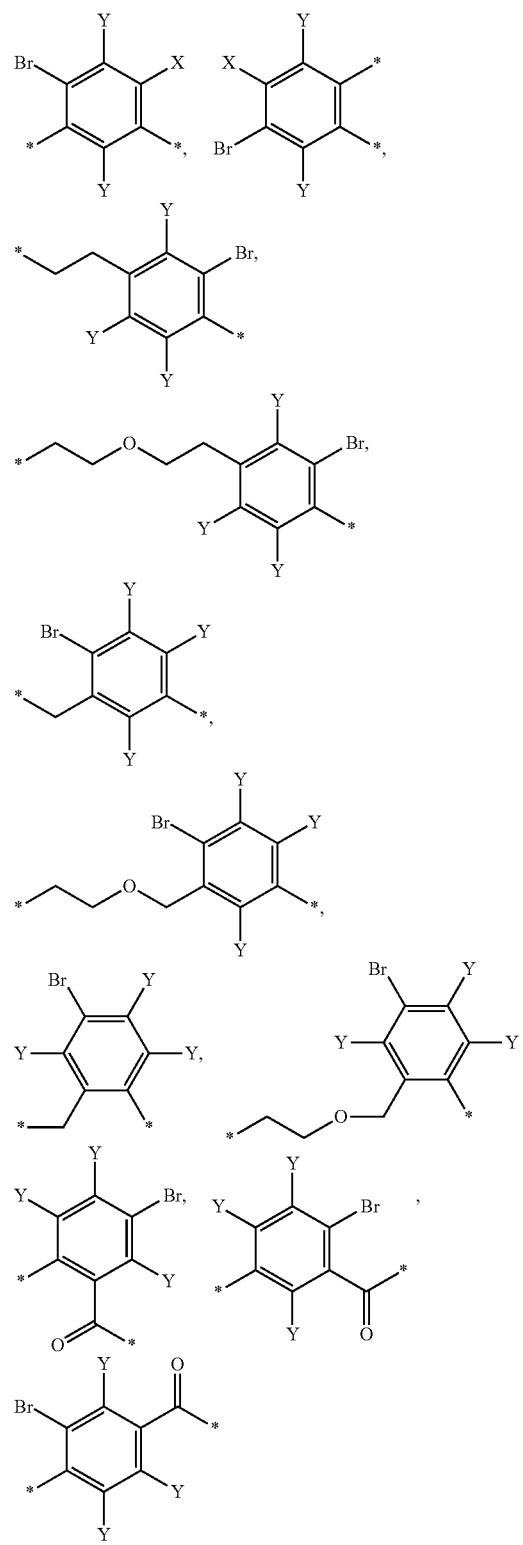

A being always attached as aryl-alkyl ether onto B and/or B', B being selected from:
 *—(CH$_2$)$_b$—*,   *—(CH$_2$—CH$_2$—O—CH$_2$—CH$_2$)—*,
 *—(CH$_2$—CH$_2$—O—CH$_2$—CH$_2$—CH$_2$)—*,
 *—(CH$_2$—CH$_2$—CH$_2$—O—CH$_2$—CH$_2$—CH$_2$)—*,

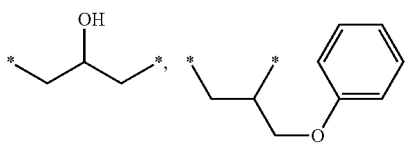

B being always attached as alkyl ester onto the (meth)acrylate reactive moiety, b=2 to 6, B' being selected from *—$(CH_2)_{b'}$—*, *—$(CH_2—CH_2—O—CH_2—CH_2)$—*,

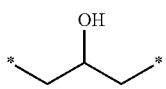

B' being always attached as alkyl ester onto the (meth)acrylate reactive moiety, b'=2 to 6, R=H, methyl, X being selected from H, methyl, ethyl, hexyl, tert-butyl, Br, Y=H, Br, "*" representing those site(s) of a moiety of the monomer, where that moiety is bonded to another moiety of the monomer.

In particular the polymerizable monomer(s) comprising a brominated resorcinol or catechol or tyrosol moiety were found to be useful.

According to one embodiment, the brominated polymerizable monomer(s) comprises a brominated resorcinol moiety according to the following formula

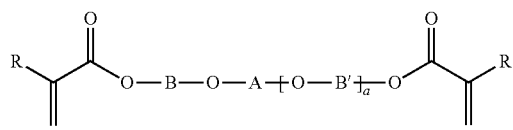

with:

B—O-A-[—O—B'-]$_a$ representing the monomer backbone as linkage between the reactive (meth)acrylate moieties, a=0 or 1, A being

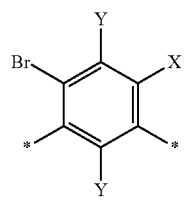

A being attached as aryl-alkyl ether onto B and/or B',

B being selected from:
*—$(CH_2)_b$—*, *—$(CH_2—CH_2—O—CH_2—CH_2)$—*,
*—$(CH_2—CH_2—O—CH_2—CH_2—CH_2)$—*,
*—$(CH_2—CH_2—CH_2—O—CH_2—CH_2—CH_2)$—*,

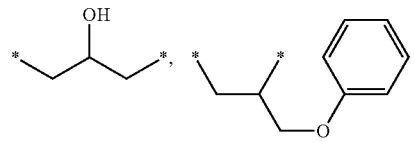

B being attached as alkyl ester onto the (meth)acrylate reactive moiety, b=2 to 6, B' being selected from *—$(CH_2)_{b'}$—*, *—$(CH_2—CH_2—O—CH_2—CH_2)$—*,

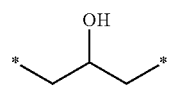

B' being attached as alkyl ester onto the (meth)acrylate reactive moiety, b'=2 to 6, R=H, methyl, X being selected from H, methyl, ethyl, hexyl, tert-butyl, Br, Y=H, Br, "*" representing those site(s) of a moiety of the monomer, where that moiety is bonded to another moiety of the monomer.

Particular examples thereof include the following monomers or mixtures thereof:

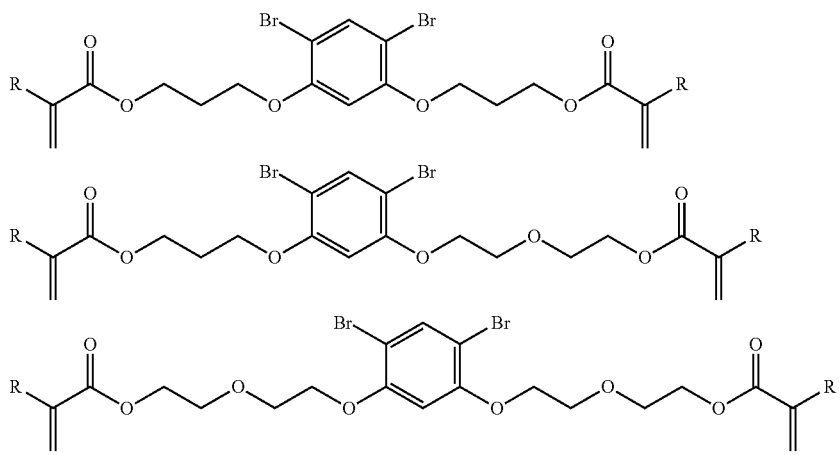

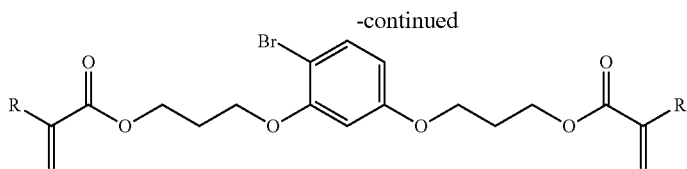

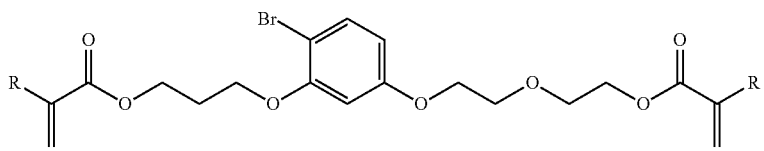

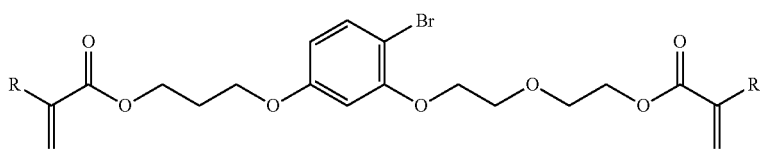

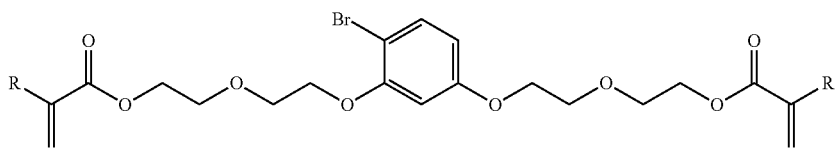

R being independently selected from H and $CH_3$.

According to one embodiment, the brominated polymerizable monomer(s) comprises a brominated catechol moiety according to the following formula

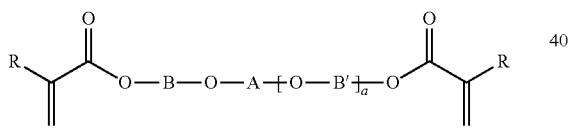

with:

B—O-A-[—O—B'-]$_a$ representing the monomer backbone as linkage between the reactive (meth)acrylate moieties, a=0 or 1, A being selected from:

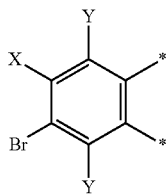

A being always attached as aryl-alkyl ether onto B and/or B',

B being selected from:

*—$(CH_2)_b$—*, *—$(CH_2$—$CH_2$—O—$CH_2$—$CH_2)$—*,
*—$(CH_2$—$CH_2$—O—$CH_2$—$CH_2$—$CH_2)$—*,
*—$(CH_2$—$CH_2$—$CH_2$—O—$CH_2$—$CH_2$—$CH_2)$—*,

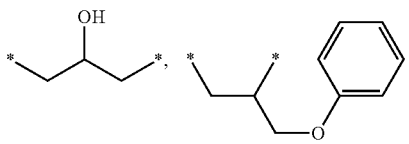

B being always attached as alkyl ester onto the (meth)acrylate reactive moiety, b=2 to 6, B' being selected from *—$(CH_2)_b$—*, *—$(CH_2$—$CH_2$—O—$CH_2$—$CH_2)$—*,

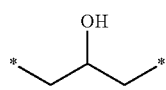

B' being always attached as alkyl ester onto the (meth)acrylate reactive moiety, b'=2 to 6, R=H, methyl, X being selected from H, methyl, ethyl, hexyl, tert-butyl, Br, Y=H, Br, "*" representing those site(s) of a moiety of the monomer, where that moiety is bonded to another moiety of the monomer.

Particular examples thereof include the following monomers or mixtures thereof:

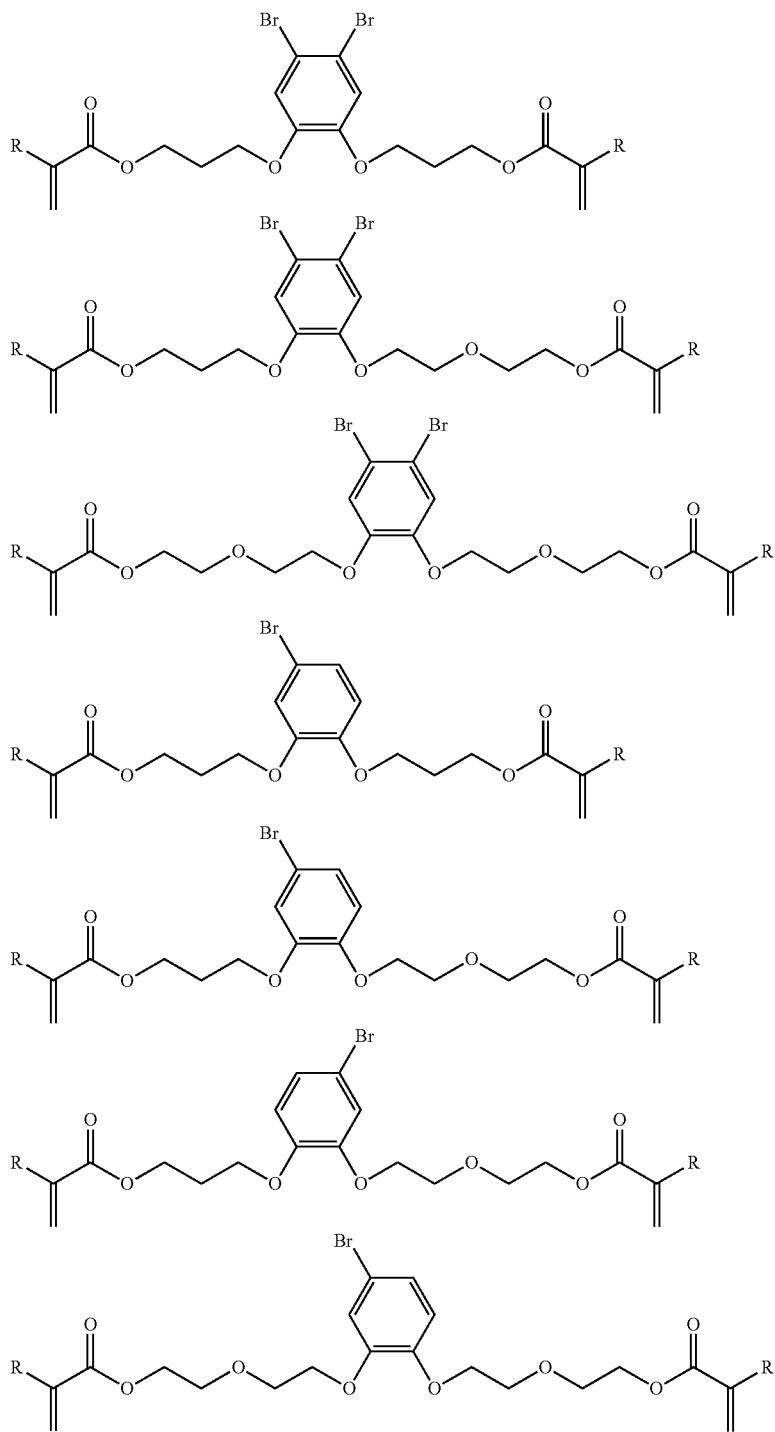
R being independently selected from H and CH$_3$.
According to one embodiment, the brominated polymerizable monomer(s) comprises a brominated tyrosol moiety according to the following formula:
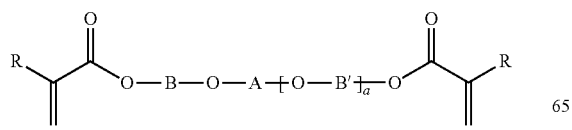

with:

B—O-A-[—O—B'-]$_a$ representing the monomer backbone as linkage between the reactive (meth)acrylate moieties, a=0 or 1, A being:

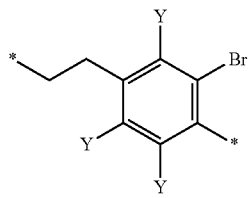

A being always attached as aryl-alkyl ether onto B and/or B',

B being selected from:

*—(CH$_2$)$_b$—*,   *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*,

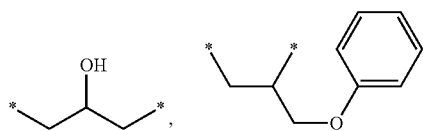 [SMILES: *CC(O)C* ; *CC(*)COc1ccccc1]

B being always attached as alkyl ester onto the (meth) acrylate reactive moiety, b=2 to 6, B' being selected from *—(CH$_2$)$_{b'}$—*, *—(CH$_2$—CH$_2$—O—CH$_2$—CH$_2$)—*,

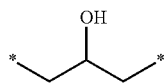

B' being always attached as alkyl ester onto the (meth) acrylate reactive moiety, b'=2 to 6, R=H, methyl, X being selected from H, methyl, ethyl, hexyl, tert-butyl, Br, Y=H, Br, "*" representing those site(s) of a moiety of the monomer, where that moiety is bonded to another moiety of the monomer.

Particular examples thereof include the following monomers or mixtures thereof:

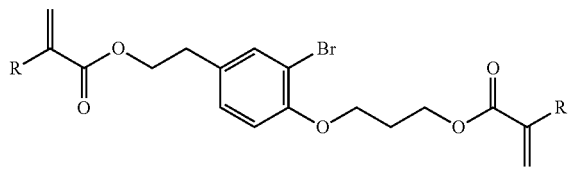

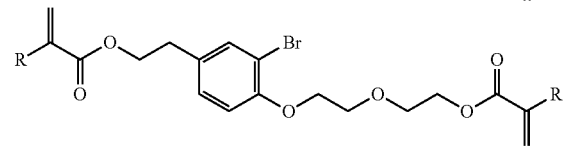

-continued

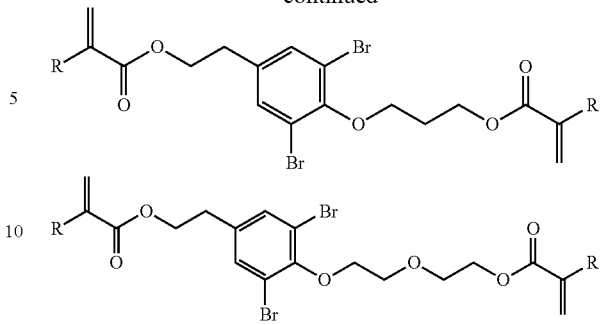

R being independently selected from H and CH$_3$

A mixture of different components according to this formula can be used as well.

A mixture of different components which was found to be particularly useful contains symmetrically substituted molecules as well as non-symmetrically substituted molecule.

The polymerizable monomers described in the present text can be synthesized e.g. as described in the example section below.

When doing so, the skilled person will realize that depending on the polymerizable monomer during synthesis a single non-symmetrical compound is obtained as well as a mixture containing different non-symmetrical components or a mixture containing minor symmetrical components besides the major non-symmetrical compound is obtained.

For a polymerizable monomer containing a non-symmetrical backbone based on a non-symmetrically substituted aromatic moiety, the synthesis will result either in a single non-symmetrical compound or in a composition containing 100 mol-% of non-symmetrical components.

Unless further purified, the synthesis of a polymerizable monomer containing a non-symmetrical backbone which is based on a symmetrically substituted aromatic moiety, will usually result—due to statistics—in a composition containing about 50 mol-% of the non-symmetrical compound as the major component besides about 25 mol-% each of symmetrical compounds as minor components. Mixtures of two, three or more of the polymerizable monomers can be used, if desired.

According to one embodiment, the brominated polymerizable monomer(s) can be further characterized by the following properties alone or in combination:
a) having a molecular weight of 400 to 800 g/mol or 450 to 700 g/mol;
b) not solidifying at 23° C.;
c) viscosity: 0.2 to 3 Pa*s at 23° C. and a shear rate of 100 1/s;
d) having a refractive index in the range of 1.52 to 1.56 or 1.53 to 1.55.

A combination of the following properties is sometime preferred: a) and b); b) and c); b) and d); a), c) and d).

A sufficiently high molecular weight can be beneficial as it reduces the risk of an undesired migration of unpolymerized monomers from the dental composition in the environment.

As the mixture of monomers has a low viscosity, filler(s) can easily be incorporated, even if no additional solvents are present.

The refractive index and colour of the monomers is beneficial, too, as it allows the formulation of aesthetic dental compositions.

Further, the brominated monomers are x-ray opaque. Thus, a dental composition containing these monomers will be x-ray opaque, too, and can make the additional incorporation of x-ray opaque filler(s) superfluous.

The brominated polymerizable monomer(s) are typically present in the following amounts:
Lower limit: at least 1 or at least 5 or at least 10 wt. %;
Upper Limit: up to 70 or up to 65 or up to 60 wt. %;
Range: 1 to 70 or 5 to 65 or 10 to 60 wt. %;
wt. % with respect to the whole composition.

The resin matrix may also contain further polymerizable monomers which are not brominated and do not comprise an acidic moiety.

If desired, such polymerizable monomers can be characterized by the following formula:

$A_nBA_m$ with A being an ethylenically unsaturated group, such as a (meth)acryloyl moiety, B being selected from (i) linear or branched $C_1$ to $C_{12}$ alkyl or alkylidene, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, 1,6 hexandiol di(meth)acrylate, 1,10 decanediol di(meth)acrylate, 1,12 dodecanediol di(meth)acrylate, trimethylolpropane tri(meth)acrylate, 1,2,4-butanetriol tri(meth)acrylate, 1,4-cyclohexanediol di(meth)acrylate, pentaerythritol tri (meth)acrylate, pentaerythritol tetraacrylate, pentaerythritol tetramethacrylate, sorbitol hexa-(meth)acrylate, bis[1-(2-(meth)acryloxy)]-p-ethoxyphenyldimethylmethane, and tri s-hydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274 (Boettcher et al.)), and acrylated oligomers (see e.g. U.S. Pat. No. 4,642,126 (Zador et al.)); and vinyl compounds such as styrene, divinyl succinate, divinyl adipate and divinylphthalate; polyfunctional (meth)acrylates comprising urethane, urea or amide groups. Mixtures of two or more of these free radically polymerizable materials can be used, if desired.

It is also possible to use the methacrylic esters mentioned in U.S. Pat. No. 4,795,823 (Schmitt et al.), such as bis[3 [4]-methacryl-oxymethyl-8(9)-tricyclo[5.2.1.0$^{2,6}$]decylmethyl triglycolate. Suitable are 2,2-bis-4(3-methacryloxy-propoxy)phenylpropane, urethane (meth)acrylates and di(meth)acrylates of bishydroxymethyltricyclo-(5.2.1.0$^{2,6}$) decane.

Further examples for polymerizable component(s) without an acidic moiety are the dimethycrylate and the diacrylate derived from tricyclodecane-dimethanol (mixture of isomers), reaction products of tricyclodecane-dimethanol with isocyanatoethyl (meth)acrylate, reaction products of tricyclodecane-diisocyanate with hydroxyethyl (meth)acrylate or hydroxypropyl (meth)acrylate. Monomers comprising a hydroxyl moiety can also be added, if desired.

Suitable compounds include 2-hydroxyethyl (meth)acrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono (meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di (meth)acrylate, 3-hydroxypropyl-1,2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth)acrylate and 2,3-dihydroxypropyl (meth)acrylate are particularly preferable.

These ethylenically unsaturated monomers can be employed in the dental composition(s) either alone or in combination with other ethylenically unsaturated monomers. If desired, mixtures of one or more of these components can be used. Monomers comprising an urethane moiety can also be added, if desired.

Suitable polymerizable monomers with an urethane moiety include those having the structure $A(-S1-U-S2-MA)_n$ with:
A being a connector element comprising at least one unit,
S1 being a spacergroup comprising at least 4 units connected with each other,
S2 being a spacergroup comprising at least 4 units connected with each other, the units of A, S1 and S2 being independently selected from —CH$_2$—, —O—, —S—, —NR$^1$—, —CO—, —CR$^1$=,

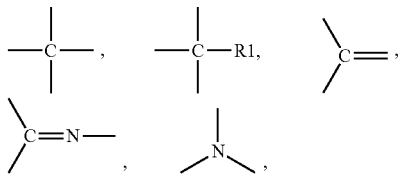

—N=, —CR$^1$R$^2$—,
with R$^1$ and R$^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups, U being an urethane, urea or amide group connecting spacergroups S1 and S2, MA being an acrylate or methacrylate group and n being 3 to 6. Specific examples of polymerizable monomers with urethane moieties include:

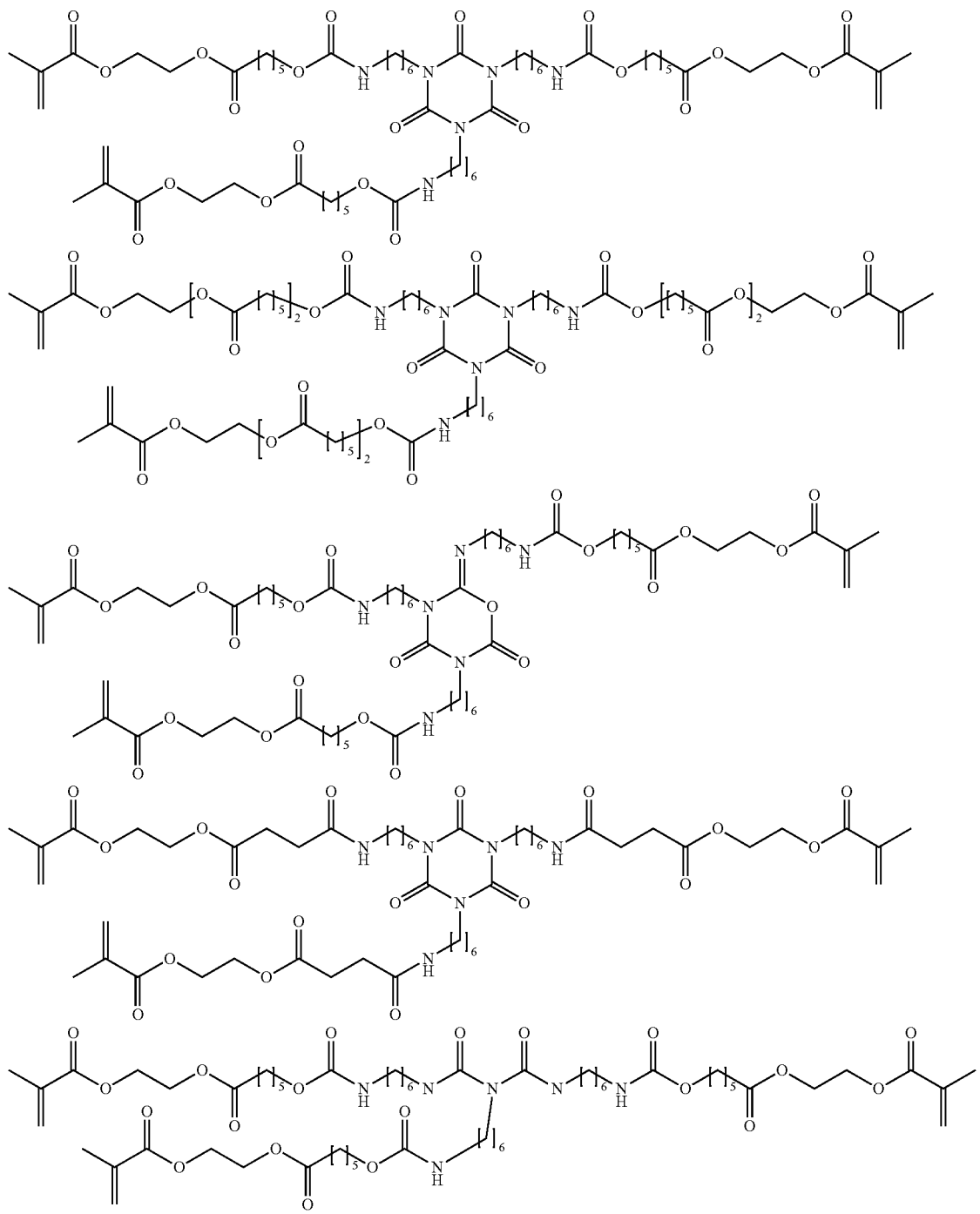

Further examples are described in U.S. Pat. No. 8,329,776 B2 (Hecht et al.). The content of this reference is herewith incorporated by reference.

In addition or besides those components, other polymerizable components which can be added include oligomeric or polymeric compounds, such as polyester urethane (meth)acrylates, polyether urethane (meth)acrylates, polycarbonate urethane (meth)acrylates and poly(meth)acrylate urethane (meth)acrylates. The molecular weight of these compounds is typically less than 20,000 g/mol, particularly less than 15,000 g/mol and in particular less than 10,000 g/mol. Adding these components may be used to adjust the rheological properties.

Mixtures of two, three or more of these non-brominated polymerizable monomers can be used, if desired.

If present, the non-brominated, non-acidic polymerizable monomers are typically present in the following amounts:
Lower limit: at least 1 or at least 5 or at least 10 wt. %;
Upper Limit: up to 65 or up to 60 or up to 55 wt. %;
Range: 1 to 65 or 5 to 60 or 10 to 55 wt. %;
wt. % with respect to the amount of the whole composition.

Besides polymerizable monomer(s) without acidic groups, the resin matrix can also comprise non-brominated polymerizable monomer(s) with acidic moieties as part of the resin matrix.

Thus, the composition described in the present text may further comprise a polymerizable monomer with an acidic moiety.

If present, the nature and structure of polymerizable monomer is not particularly limited, either unless the desired result cannot be achieved.

The presence of polymerizable monomer can be beneficial because it can provide the composition with a desired acidity.

The polymerizable components with acid moiety can typically be represented by the following formula $$A_n BC_m$$

with A being an ethylenically unsaturated group, such as a (meth)acryloyl moiety, B being a spacer group, such as (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and C being an acidic group, m, n being independently selected from 1, 2, 3, 4, 5 or 6, wherein the acidic group comprises one or more carboxylic acid or anhydride residues, such as —COOH or —CO—O—CO—, phosphoric acid residues, such as —O—P(O)(OH)OH, phosphonic acid residues, such as C—P(O)(OH)(OH), sulfonic acid residues, such as —SO₃H or sulfinic acid residues such as —SO₂H.

Examples of polymerizable components with acid moiety include, but are not limited to glycerol phosphate mono(meth)acrylate, glycerol phosphate di(meth)acrylate, hydroxyethyl (meth)acrylate (e.g., HEMA) phosphate, bis((meth)acryloxyethyl) phosphate, (meth)acryloxypropyl phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Derivatives of these hardenable components bearing an acid moiety that can readily react e.g. with water to form the specific examples mentioned above, like acid halides or anhydrides are also contemplated.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Using (meth)acrylate functionalized polyalkenoic acids is often preferred as those components were found to be useful to improve properties like adhesion to hard dental tissue, formation of a homogeneous layer, viscosity, or moisture tolerance.

According to one embodiment, the composition contains (meth)acrylate functionalized polyalkenoic acids, for example, AA:ITA:IEM (copolymer of acrylic acid:itaconic acid with pendent methacrylates).

These components can be made by reacting e.g. an AA:ITA copolymer with 2-isocyanatoethyl methacrylate to convert at least a portion of the acid groups of the copolymer to pendent methacrylate groups. Processes for the production of these components are described, e.g., in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.). The content of these references is herewith incorporated by reference.

Mixtures of two, three or more of the polymerizable monomers with acidic moieties can be used, if desired.

If present, the non-brominated polymerizable monomer with acidic moieties can be present in the following amounts:

Lower limit: at least 1 or at least 5 or at least 10 wt. %;
Upper Limit: up to 50 or up to 40 or up to 30 wt. %;
Range: 1 to 50 or 5 to 40 or 10 to 30 wt. %;
wt. % with respect to the amount of the whole composition.

The dental composition described in the present text comprises an initiator system.

The initiator system is suitable for starting the curing of the polymerizable monomers contained in the resin matrix. The initiator system can comprise one or more initiators.

The nature of the initiator is not particularly limited, unless the desired result cannot be achieved.

The initiator system can comprise systems which are capable of initiating polymerization via radiation (i.e. radiation curing), heat (i.e. heat curing), redox reaction (i.e. redox-curing) or a combination thereof.

A class of initiators capable of initiating polymerization of the hardenable components of the resin matrix which contain free radically active functional groups includes free radical-generating photoinitiators, optionally combined with a photosensitizer or accelerator.

Such initiators typically can be capable of generating free radicals for addition polymerization upon exposure to light energy having a wavelength between about 200 and about 700 nm. Initiator components which can undergo an alpha-cleavage are sometimes preferred.

Using acylphosphine oxides as initiators or part of the initiator system was found to be particularly useful.

Suitable acylphosphine oxides can be characterized by the following formula:

$$(R^9)_2\text{—P(=O)—C(=O)—}R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a —Z—C(=O)—P(=O)—(R⁹)₂ group, wherein Z represents a divalent hydrocarbyl group such as alkylene or phenylene having from 2 to 6 carbon atoms.

Suitable systems are also described e.g. in U.S. Pat. No. 4,737,593 (Ellrich et al.), the content of which is herewith incorporated by reference.

Preferred acylphosphine oxides useful in the invention are those in which the R⁹ and R¹⁰ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is 2,4,6-trimethylbenzoyl diphenyl phosphine oxide (Lucirin™ TPO, BASF).

Suitable bisacylphosphine oxides can also be described by the following formula:

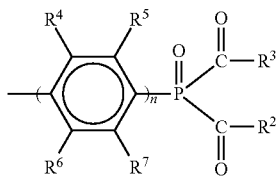

wherein n is 1 or 2, and R⁴, R⁵, R⁶ and R⁷ are H, C1-4 alkyl, C1-4 alkoxyl, F, Cl or Br; R² and R³, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or R² and R³ are joined to form a ring containing from 4 to 10 carbon atoms and being optionally substituted by 1 to 6 C1-4 alkyl radicals.

More specific examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (formerly known as IRGACURE™ 819, Ciba Specialty Chemicals, Tarrytown, N.Y.) is sometimes preferred.

Tertiary amine reducing agents may be used in combination with an acylphosphine oxide. Illustrative tertiary amines useful in the invention include ethyl 4-(N,N-dimethylamino)benzoate (EDMAB) and N,N-dimethylaminoethyl methacrylate (DMAEMA).

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (formerly known as IRGACURE™ 1700, Ciba Specialty Chemicals), 2-benzyl-2-(N,N-dimethylamino)-1-(4-morpholinophenyl)-1-butanone (formerly known as IRGACURE™ 369, Ciba Specialty Chemicals), bis(η5-2,4-cyclopentadien-1-yl)-bis(2,6-difluoro-3-(1H-pyrrol-1-yl)phenyl) titanium (formerly known as IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (formerly known as DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

A variety of visible or near-IR photoinitiator systems may also be used for photopolymerization of free-radically polymerizable materials.

For example, a photoinitiation system can be used selected from systems which initiate polymerization via a two-component system of an amine and an α-diketone. Such systems are described e.g. in U.S. Pat. No. 4,071,424 (Dart et al.) and WO 2009/151957, which are herein incorporated by reference.

Alternatively, the resin can be combined with a three components or ternary photoinitiator system. Suitable systems are described in U.S. Pat. No. 5,545,676 (Palazzotto et al.) and WO 2009151957, which are incorporated herein by reference.

In the ternary photoinitiator system, the first component is an iodonium salt, i.e., a diaryliodonium salt. The iodonium salt is preferably soluble in the monomer and shelf-stable (i e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313 (Smith), U.S. Pat. No. 3,741,769 (Smith), U.S. Pat. No. 3,808,006 (Smith), U.S. Pat. No. 4,250,053 (Smith) and U.S. Pat. No. 4,394,403 (Smith), the iodonium salt disclosures of which are incorporated herein by reference. The iodonium salt can be a simple salt (e.g., containing an anion such as Cl⁻, Br⁻, I⁻ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nm and most preferably greater than 400 to 600 nanometers. The sensitizer may also be capable of sensitizing 2-methyl-4,6-bis(trichloromethyl)-s-triazine, using the test procedure described in U.S. Pat. No. 3,729,313 (Smith), which is incorporated herein by reference.

Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below 1000, more preferably below 100, at the desired wavelength of irradiation for photopolymerization.

Alternatively, dyes that exhibit reduction in light absorption at the excitation wavelength upon irradiation can be used.

For example, a preferred class of ketone sensitizers has the formula: $ACO(X)_b B$, where X is CO or $CR^5R^6$, where $R^5$ and $R^6$ can be the same or different, and can be hydrogen, alkyl, alkaryl or aralkyl, b is zero or one, and A and B can be the same or different substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like.

Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxybenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676 (Palazzotto et al.), which is incorporated herein by reference.

Another free-radical initiator system that can alternatively be used in the dental compositions described in the present text is the class of ionic dye counterion complex initiators comprising a borate anion and a complementary cationic dye.

Borate salt photoinitiators are described, for example, in U.S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.). The disclosures of these references is herewith incorporated by reference.

Borate anions useful in these photointiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri (2-pyridyl-s-triazine) and related ligands.

Yet another alternative class of initiators capable of initiating polymerization of free radically active functional groups includes conventional chemical initiator systems such as a combination of a peroxide and an activator such as an amine.

These initiators, which rely upon a thermal redox reaction, are often referred to as "auto-cure catalysts." They are typically supplied as two-part systems in which the reactants are stored apart from each other and then combined immediately prior to use.

In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 (Taylor) as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967

(Hecht et al.), U.S. Pat. No. 3,347,954 (Bredereck et al.) as well as the malonyl sulfamides described in U.S. Pat. No. 4,544,742 (Schmitt et al.). Preferred malonyl sulfamides are 2,6-dimethyl-4-isobutylmalonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

In a further alternative, heat may be used to initiate the hardening, or polymerization, of free radically active groups. Examples of heat sources suitable for the dental materials described in the present text include inductive, convective, and radiant. Thermal sources should be capable of generating temperatures of at least 40° C. to 15° C. This procedure is sometime preferred for initiating polymerization of materials occurring outside of the oral environment.

Yet another alternative class of initiators capable of initiating polymerization of free radically active functional groups that are useful for the dental materials as described in the present text are those that include free radical-generating thermal initiators. Examples include peroxides such as, for example, benzoyl peroxide and lauryl peroxide, and azo compounds such as, for example, 2,2-azobis-isobutyronitrile (AIBN).

If the colour of the cured composition matters, an initiator system which does not lead to undesired discolouration should be used. It was found that an initiator system comprising the following components is particularly useful: monoacylphosphine oxides and/or bisacylphosphine oxides.

The initiator or initiator system is typically contained in the following amounts:
Lower limit: at least 0.1 or at least 0.2 or at least 0.3 wt. %;
Upper Limit: up to 10 or up to 8 or up to 6 wt. %;
Range: 0.1 to 10 or 0.2 to 8 or 0.3 to 6 wt. %;
wt. % with respect to the whole composition.

The dental composition described in the present text comprises a filler system.

The filler system comprises at least 25 wt. % of the weight of the dental composition.

The filler system can comprise one filler or different kinds of fillers. Sometimes, using a mixture of different fillers can be preferred.

Adding a filler can be beneficial e.g. for adjusting the rheological properties like viscosity. The content of the filler also typically influences the physical properties of the composition after hardening, like hardness or flexural strength.

The chemical nature of the filler(s) is not particularly limited unless the intended purpose cannot be achieved.

The size of the filler particles should be such that a homogeneous mixture with the polymerizable component(s) forming the resin matrix can be obtained.

The particle size of the filler particles may be in a range of 0.001 to 10 µm.

If desired, the mean particle size can be determined by light scattering using e.g. a Malvern Mastersizer™ 2000 device available from Malvern Instruments.

The filler(s) typically comprise non acid reactive fillers. A non-acid reactive filler is a filler which does not undergo an acid/base reaction with an acid.

Useful non acid reactive fillers include quartz, cristobalite, ground glasses, calcium silicate, zirconium silicate, non-water-soluble fluorides such as $CaF_2$, silica gels, fumed silica in particular pyrogenic silicic acid and granulates thereof.

The filler system is typically present in the following amounts:
Lower limit: at least 25 or at least 30 or at least 35 wt. %;
Upper Limit: up to 90 or up to 85 or up to 80 wt. %;
Range: 25 to 90 or 30 to 85 or 35 to 80 wt. %;
wt. % with respect to the whole composition.

Filler(s) which can also be used include nano-fillers such as nano-sized silica.

The nano-filler(s) can be selected from aggregated, agglomerated or discrete (i.e. non-agglomerated, non-aggregated) nano-sized particles or mixtures thereof. It was found that compared to other fillers, using nano-filler(s) can be beneficial because it allows for the formulation of a composition with high filler load resulting in better mechanical properties, e.g. polishability or abrasion and in higher aesthetics.

According to one embodiment, the nano-filler(s) comprises aggregated nano-sized particles.

The nano-filler comprising aggregated nano-sized particles can typically be characterized by at least one or all of the following features:
Specific surface (BET according to Brunauer, Emmet and Teller): 30 to 400 or 60 to 300 or 80 to 250 $m^2/g$;
comprising particles of $SiO_2$, $ZrO_2$, $Al_2O_3$ and mixtures thereof.

If desired, the specific surface can be determined according to Brunauer, Emmet and Teller (BET; e.g. by using a device like Monosorb™ available from Quantachrome).

A suitable nano-filler comprising aggregated nano-sized particles can be produced according to the processes described e.g. in U.S. Pat. No. 6,730,156 (Windisch et al.) (preparatory example A).

A useful nano-filler comprising aggregated nano-sized particles can be prepared from a suitable sol and one or more oxygen containing heavy metal compound solution(s) precursors which may be salts, sols, solutions, or nano-sized particles; of these, sols are preferred. For purposes of this text, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties:
a) the average size of the individual particles, which is preferably less than 100 nm in diameter, b) the acidity: the pH of the sol should be preferably below 6 and more preferably below 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability of a dental restoration made out of a composite comprising such nanoparticles.

If the starting sol is basic, it should be acidified e.g. by addition of nitric or other suitable acid to decrease the pH. However, choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is 0.5:1 to 10:1, more preferably 3:1 to 9:1, and most preferable 4:1 to 7:1.

In a preferred embodiment where the aggregated nano-sized particles contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of 1.5 to 4.0.

The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at 200° C. to 800° C., more preferably 300° C. to 600° C. Soaking is performed for 0.5 hours to 8 hours, depending on the amount of material being calcined. It is preferred that the soak time of the calcine step be such that a plateaued surface area is obtained. It is preferred that the time and temperature be chosen such that the resulting filler is white in color, free from black, grey, or amber colored particles, as determined by visual inspection.

The calcined material is then preferably milled to a median particle size of less than 5 μm, preferably less than 2 μm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is the preferred method.

The resulting fillers comprise, contain, consist essentially or consist of aggregated nano-sized particles. If desired, this can be proven by transmission electron microscopy (TEM).

If desired, the surface of the filler particles can be surface treated. The surface-treatment can be accomplished according to a process as described in U.S. Pat. No. 6,730,156 (Windisch et al.) (e.g. preparatory example B).

Once dispersed in the resin, the filler remains in an aggregated stage. That is, during the dispersion step the particles do not break up into discrete (i.e. individual) and un-associated (i.e. non-aggregated) particles.

If present, the nano-filler comprising aggregated nano-sized particles is typically present in either of the following amounts:
  at least 20 or at least 30 or at least 40 wt. %;
  utmost 70 or utmost 60 or utmost 50 wt. %;
  20 to 70 or 30 to 60 or 40 to 50 wt. %;
  wt. % with respect to the weight of the dental composition.

According to one embodiment, the nano-filler(s) comprises agglomerated nano-sized particles.

Nano-filler(s) comprising agglomerated nano-sized particles are typically characterized by at least one or all of the following features:
  Specific surface (BET according to Brunauer, Emmet and Teller): 30 to 400 or 50 to 300 or 70 to 250 m$^2$/g;
  comprising particles of $SiO_2$, $ZrO_2$, $Al_2O_3$ and mixtures thereof.

If desired, the specific surface can be determined as described above.

Suitable agglomerated nanoparticles include fumed silicas such as products sold under the tradename Aerosil™ e.g. Aerosil™ OX-130, -150, and -200, Aerosil™ R8200 available from Degussa AG, (Hanau, Germany), CAB-O-SIL™ M5 available from Cabot Corp (Tuscola, Ill.), and HDK™, e.g. HDK-H 2000, HDK H15; HDK H18, HDK H20 and HDK H30 available from Wacker Company.

The surface of the filler particles can be treated with a resin-compatibilizing surface treatment agent.

Particularly preferred surface treatment or surface modifying agents include silane treatment agents capable of polymerizing with a resin. Preferred silane treatment agent include γ-methacryloxylpropyltrimethoxysilane, available commercially under the trade designation A-174 from Witco OSi Specialties (Danbury, Conn.) and γ-glycidoxypropyltrimethoxy silane, a product available under the trade designation G6720, available from United Chemical Technologies (Bristol, Pa.).

Alternatively, a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, cycloalkyl, hydroxy alkyl, aryl, hydroxy aryl, or amino alkyl functional silanes.

If present, the nano-filler comprising agglomerated nano-sized particles is typically present in either of the following amounts:
  at least 1 or at least 3 or at least 5 wt. %;
  utmost 20 or utmost 15 or utmost 10 wt. %;
  1 to 20 or 3 to 15 or 5 to 10 wt. %;
  wt. % with respect to the weight of the dental composition.

According to one embodiment, the nano-filler(s) comprises non-agglomerated, i.e. discrete nano-sized particles.

Discrete nano-sized particles which can be used are preferably substantially spherical and substantially non-porous.

Nano-filler(s) comprising discrete nano-sized particles are typically characterized by at least one or all of the following features:

Average particle diameter: less than 200 nm or less than 100 nm;

comprising particles of $SiO_2$, $ZrO_2$ and mixtures thereof.

Preferred nano-sized silicas are commercially available from Nalco Chemical Co. (Naperville, Ill.) under the product designation NALCO™ COLLOIDAL SILICAS. For example, preferred silica particles can be obtained from using NALCO™ products 1040, 1042, 1050, 1060, 2327 and 2329.

If desired, the measurement of the particle size of the nano filler particles can be done with a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

If present, the discrete nano-sized particles are typically present either of the following amounts:
at least 1 or at least 3 or at least 5 wt. %;
utmost 30 or utmost 25 or utmost 20 wt. %;
1 to 30 or 3 to 25 or 5 to 20 wt. %;
wt. % with respect to the weight of the dental composition.

According to one embodiment, the dental composition comprises:
aggregated nano-sized particles in an amount of 20 to 70 wt. %,
agglomerated nano-sized particles in an amount of 1 to 20 wt. %,
discrete nano-sized particles in an amount of 1 to 30 wt. %,
wt. % with respect to the weight of the whole composition.

Besides an inorganic material the filler(s) can also comprise an organic material.

Examples of suitable organic filler particles include filled or unfilled pulverized polycarbonates, poly(meth)acrylates, polyepoxides, and the like.

The amount of filler to be used in the filler matrix usually depends on the purpose for which the composition should be used.

The dental composition described in the present text may also comprise additive(s).

Additive(s) which may be present include pigments, photobleachable colourants, fluoride release agents, stabilizers, retarders, plasticizers, flavorants, anti-microbials, fragrance, agents that impart fluorescence and/or opalescence and fluoride releasing materials and mixtures thereof.

Examples of pigments, which can be used include titanium dioxide or zinc sulphide (lithopones), red iron oxide 3395, Bayferrox™ 920 Z Yellow, Neazopon™ Blue 807 (copper phthalocyanine-based dye) or Helio™ Fast Yellow ER. These additives may be used for individual colouring of the dental compositions.

Examples of photobleachable colourants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colourants can be found in U.S. Pat. No. 6,444,725 (Trom et al.).

Examples of fluoride release agents which can be present include naturally occurring or synthetic fluoride minerals. These fluoride sources can optionally be treated with surface treatment agents.

Further additives, which can be added, include stabilizers, Oral Carecially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4', 6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, and silicone oils), flavorants, anti-microbials, fragrance, agents that impart fluorescence and/or opalescence and fluoride releasing materials.

There is no need for the additive(s) to be present. The additive(s) may be present in the following amounts:
Lower limit: at least 0 or at least 0.1 or at least 1 wt. %;
Upper Limit: up to 10 or up to 8 or up to 5 wt. %;
Range: 0 to 10 or 0.1 to 8 or 1 to 5 wt. %;
wt. % with respect to the whole composition.

According to one embodiment, the dental composition is characterized by comprising:
the resin matrix: 5 to 70 wt. %, or 10 to 70 wt. %,
the filler matrix: 25 to 90 wt. %, or 30 to 80 wt. %,
the initiator system: 0.1 to 10 wt. %, or 0.5 to 8 wt. %,
wt. % with respect to the weight of the whole composition.

According to another embodiment, the dental composition is characterized by comprising:
the resin matrix: 5 to 70 wt. %, comprising
brominated polymerizable monomer(s) according to formula (I) described above, in an amount of 1 to 50 wt. %;
non-brominated, non-acidic polymerizable monomer(s), preferably in an amount of 1 to 50 wt. %;
non-brominated, acidic polymerizable monomer(s), preferably in an amount of 1 to 50 wt. %;
the filler matrix: 30 to 90 wt. %,
the initiator system: 0.1 to 10 wt. %.

According to a further embodiment, the dental composition comprises:
a resin matrix in an amount of 5 to 75 wt. % comprising
brominated polymerizable monomer(s) according to formula (I)

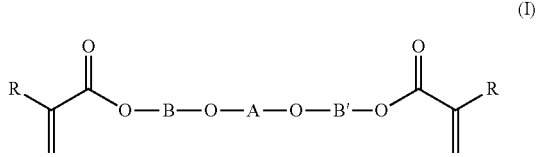

(I)

with
B—O-A-O—B' representing the monomer backbone as linkage between reactive (meth)acrylate moieties,
A being selected from

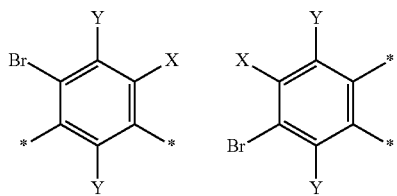

A being attached as aryl-alkyl ether onto B and B',
B being independently selected from:
*—(CH$_2$)$_b$—*, *—(CH$_2$—CH$_2$—O—CH$_2$—CH$_2$)—*, *—(CH$_2$—CH$_2$—O—CH$_2$—CH$_2$—CH$_2$)—*, *—(CH$_2$—CH$_2$—CH$_2$—O—CH$_2$—CH$_2$—CH$_2$)—*,

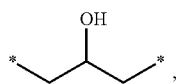

B being attached as alkyl ester onto the (meth)acrylate reactive moiety,
b=2 to 6,
B' being independently selected from
*—(CH$_2$)$_{b'}$—*, *—(CH$_2$—CH$_2$—O—CH$_2$—CH$_2$)—*,

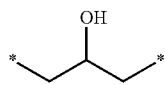

B' being attached as alkyl ester onto the (meth)acrylate reactive moiety,
b'=2 to 6,
R=H, methyl,
X being independently selected from H, C$_{1-6}$ alkyl, Br,
Y=H, Br,
"*" representing those site(s) of a moiety of the monomer, where that moiety is bonded to another moiety of the monomer, and
non-brominated, non-acidic polymerizable monomers,
a filler matrix in an amount of 25 to 90 wt. % comprising nano-fillers selected from aggregated nano filler(s), agglomerated nano filler(s), discrete nano filler(s), and mixtures thereof,
an initiator system comprising
radiation curing initiator(s), redox-curing initiator(s) and combinations thereof, wt. % with respect to the weight of the whole composition, wherein the components are as defined in the present text and the claims.

All components used in the dental composition described in the present text should be sufficiently biocompatible, that is, the dental composition should not produce a toxic, injurious, or immunological response in living tissue.

According to one embodiment, the dental composition described in the present text does not contain or is essentially free of the following components:
solvent(s) selected from water or alcohol(s) (e.g. C$_1$ to C$_4$ alcohols such as ethanol) or combinations thereof in an amount of more than 5 or 10 wt. %;
bisphenol A-glycidyl methacrylate in an amount of more than 5 or 10 wt. %;
wt. % with respect to the weight of the whole composition.

The dental composition described in the present text can be produced as follows:
a) providing the respective components,
b) mixing the components.

Mixing can be achieved by using any means known to the practitioner. That is, the adhesive composition can be prepared in a one-pot synthesis simply by putting the respective components together and mixing them.

If desired, the production process is performed under save light conditions to avoid an undesired polymerization of the composition.

The temperature used should be below the boiling point of the composition at normal pressure (1013 mbar). Usually the process can be conducted at a temperature in the range of 5° C. to 100° C. or within a range of 10° C. to 80° C. Conducting the process under ambient temperature (e.g. about 23° C.) has been found possible as well.

The atmosphere under which the process of the invention can be conducted is not particularly limited, either.

Usually, the processes are conducted under ambient conditions. Depending on the components used, conducting the process under inert conditions can be recommended. In this respect a nitrogen or argon atmosphere could be useful.

The pressure under which the process of the invention can be conducted is not particularly limited, either. However, the process is typically conducted under ambient pressure (about 1013 mbar).

The dental composition described in the present text is typically stored in a container until use. Depending on the formulation and the curing status, various containers can be used.

The composition can be provided in the form of a one-component system or as a two-component system. This typically depends on the initiator system chosen. If the composition is redox curable or curing, it is usually provided as a two-component system.

If the dental composition is provided as a one-component system, it can be stored in a container having only one chamber such as a compule or screw tube.

A compule typically has a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260 (Wilcox et al.), EP 1 340 472 A1 (Centrix), US 2007/0172789 A1, U.S. Pat. No. 5,893,714 (Arnold et al.) and U.S. Pat. No. 5,865,803 (Major). The content of these references with regard to the description of compules or containers is herewith incorporated by reference.

Suitable two-component systems for storage include two-barrel cartridges.

Suitable two-component systems are described e.g. in US 2007/0090079 (Keller) or U.S. Pat. No. 5,918,772 (Keller et al.). The content of these documents with respect to the description of the vial or bottle is herewith incorporated by reference. Cartridges which can be used are also commercially available from SulzerMixpac AG (Switzerland).

The volume of each compartment of the two-barrel cartridges is typically in the range of 0.1 to 100 ml or 0.5 to 50 ml or 1 to 30 ml.

The volume ratio of compartment (I) to compartment (II) is typically within a range of 1:1 to about 10:1.

Static mixing tips which can be used for mixing the compositions contained in the compartments are described e.g. in US 2006/0187752 (Keller) or in U.S. Pat. No. 5,944,419 (Streif). The disclosure of these patents is herewith incorporated by reference. Mixing tips which can also be used are commercially available from SulzerMixpac AG (Switzerland).

If the dental composition is provided in the form of a dental mill blank, it is typically fixed to a holding device including frames or mandrels.

The invention described in the present text is also directed to a kit of parts.

Such a kit typically comprises the dental composition described in the present text, a dental adhesive and/or a dental cement, optionally an applicator and optionally an instruction of use.

The instruction of use typically contains hints to the practitioner how and under what conditions the adhesive composition should be applied to the surface of hard dental tissue.

The dental composition can be used as or for producing a dental restorative material, dental cement, dental crown or bridge material or dental mill blank.

The dental composition is typically used in the mouth of a patient and is disposed adjacent to natural teeth. The phrase "disposed adjacent to" as used herein refers to the placing of a dental material in temporary or permanent (e.g., occlusal or proximal) contact with a natural tooth.

The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth.

A typical application process for the composition described in the present text to be used as a restorative composite typically includes the following steps in the desired order:
  providing the dental composition,
  placing the dental composition in contact with hard dental tissue, especially the surface thereof,
  curing the dental composition, e.g. by applying radiation (e.g. visible light) to the composition for a period of time sufficient to initiate the polymerisation process (e.g. 5 to 20 s).

Suitable tools for applying radiation include dental curing lights. Suitable dental curing lights are described e.g. in US 2005/0236586 (Hartung). The content of this document is herewith incorporated by reference. Suitable dental curing lights are also commercially available e.g. under the trade names Elipar™ S10 (3M Oral Care).

The dental composition described in the present text can also be used for producing a dental crown, bridge, onlay or inlay outside the mouth of a patient.

The production can be done either by a so-called constructive approach (i.e. build-up approach) or by a so-called destructive approach (i.e. machining or milling approach).

The build-up approach can be performed by any means known to the skilled person including rapid-prototyping techniques.

Rapid-prototyping techniques include ink-jet printing, 3d-printing, robo-casting, laminated object manufacturing, stereolithography, photostereolithography, or combinations thereof.

The machining approach can also be performed by any means known to the skilled person including milling the desired dental restoration out of a dental mill blank.

If desired, the dental mill blank can be attached to a holding device.

Suitable holding devices include frames and stubs or mandrels. Sometimes it can be desirable, if the dental mill blank is put in a magazine, either for storing or for machining. The holding device typically facilitates the machining of the dental article, e.g. by using a machining or milling device.

Examples of holding devices are shown in US 2003/0132539 (Althoff et al.), U.S. Pat. No. 6,769,912 (Beuschel et al.) and EP 0 455 854 B1 (Pfeiffer et al.). The content of these documents with regard to holding devices (e.g. frames and stubs or supporting body) is herewith incorporated by reference and regarded part of the text of the present invention.

Fixing of the dental mill blank to the holding device can be achieved e.g. by gluing. The fixing should be such that the dental milling blank can be processed in a milling machine.

Besides gluing other means for attaching the holding device include bonding, screwing, and combinations thereof.

The dental mill blank can be produced as follows:
a) providing a dental composition as described in the present text, the dental composition being in its uncured state,
b) hardening or curing the dental composition to obtain a hardened or cured dental composition,
c) optionally fixing the hardened dental composition to a holding device, the dental composition being provided in the shape of a dental mill blank.

The dental mill blank can be produced by placing the curable dental composition into a mould followed by a curing step.

Another option for producing a dental mill blank is to apply a build-up or layer technique. In that case, the dental composition is typically provided in the form of a flat layer, the layer is cured and a further curable layer of the dental composition is applied on top of the previous layer followed by a further curing step. These steps are repeated until the object has the desired dimensions.

A dental restoration can be produced as follows:
a) providing a dental mill blank as described in the present text, the dental mill blank comprising the dental composition described in the present text, the dental composition being in its cured state,
b) machining the dental mill blank to obtain a dental restoration, the dental restoration having typically the shape of a dental crown, bridge, inlay or veneer.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention.

The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate the invention.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar). Moreover, nearly all process steps are conducted under an atmosphere of dry air.

Methods

Viscosity

If desired, the viscosity can be determined under the following conditions: 23° C.; shear rate: 100 l/s; measured with a cone/plate geometry CP25-1 with a Physica MCR 301 Rheometer, Anton Paar GmbH, Graz, Austria.

Refractive Index ($n_D^{20}$)

If desired, the refractive index can be measured with a Kruess AR 4 D device (refractometer according to Abbe's measure principle). The refractive index is typically measured at 20.0° C. at a wavelength of 589 nm.

Storage Stability

A composition is considered as storage stable, if the components of the composition do not settle during storage for 3 months and if the physical mechanical properties of the composition after hardening do not change by more than 20% after 3 months of storage compared to the physical mechanical properties determined shortly after the preparation of the composition.

Flexural Strength (FS)

If desired, the measurement of the flexural strength can be carried out according to ISO 4049 using a universal testing machine (Zwick Z 010, crosshead speed 1 mm/min). The flexural strength is typically given in MPa.

E-Modulus (E-M)

If desired, the E-M (I) can be determined according to ISO 4049:2009(E) and is given in [GPa].

Abbreviations

The name and/or structure of the components used are given in Table 1.

TABLE 1

| | | |
|---|---|---|
| E4R-A/MA/AM | [structure: R–C(=O)–O–CH₂CH₂–O–CH₂CH₂–O–(phenyl)–O–CH₂CH₂–O–CH₂CH₂–O–C(=O)–R]<br>R = CH₃: E4R-MA | CE1 |
| ÖR-A/MA/AM | mixture consisting of OR-A/MA/AM, OE2R-A/MA/AM, and E4R-A/MA/AM:<br>[structure 1: R–C(=O)–O–CH₂CH₂CH₂–O–(phenyl)–O–CH₂CH₂CH₂–O–C(=O)–R]<br>[structure 2: R–C(=O)–O–CH₂CH₂CH₂–O–(phenyl)–O–CH₂CH₂–O–CH₂CH₂–O–C(=O)–R]<br>[structure 3: R–C(=O)–O–CH₂CH₂–O–CH₂CH₂–O–(phenyl)–O–CH₂CH₂–O–CH₂CH₂–O–C(=O)–R]<br>R = CH₃: ÖR-MA | CE2 |
| DiBrE4R-A/MA/AM | [structure: R–C(=O)–O–CH₂CH₂–O–CH₂CH₂–O–(dibromophenyl)–O–CH₂CH₂–O–CH₂CH₂–O–C(=O)–R]<br>R = CH₃: DiBrE4R-MA | IE1 |

TABLE 1-continued

| | | |
|---|---|---|
| DiBrÖR-A/MA/AM | mixture of DiBrOR-A/MA/AM, DiBrOE2R-A/MA/AM, and DiBrE4R-MA/A/AM | IE2 |

R = H: DiBrÖR-A; R = CH₃: DiBrÖR-MA,; R = 1x H/1x CH₃: DiBrÖR-AM

| | | |
|---|---|---|
| Resorcinol | 1,3-dihydroxybenzene, CAS 108-46-3, EC 203-585-2 | R |
| Oxetanylated resorcinol (and brominated analogues) | (monobrominated analogue; BrOR, dibrominated analogue; DiBrOR) | OR, (BrOR, DiBrOR) |
| Ethoxylated(2) oxetanylated resorcinol (and brominated analogues) | (monobrominated analogue; BrOE2R, dibrominated analogue; DiBrOE2R) | OE2R, (BrOE2R, DiBrOE2R) |
| Ethoxylated(4) resorcinol (and brominated analogues) | (monobrominated analogue: BrE4R, dibrominated analogue: DiBrE4R) | E4R, (BrE4R, DiBrE4R) |
| Mixtures | mixture consisting of OR, OE2R, and E4R (monombrominated analogue BrÖR: BrOR, BrOE2R, and BrE4R; dibrominated analogue DiBrÖR: DiBrOR, DiBrOE2R, and DiBrE4R) | ÖR, (BrÖR, DiBrÖR) |
| Acrylic acid | Propenoic acid, CAS 79-10-7, EC 201-177-9 | AA |
| Methacrylic acid | 2-Methacrylic acid, 2-Methylpropenoic acid, CAS 79-41-4, EC 201-204-4 | MA |
| Methane sulfonic acid | CAS 75-75-72, EC 200-898-6 | MSA |
| iso-Propanol | 2-propanol, CAS 67-63-0, EC 200-661-7 | IPA |
| tert-Butanol | 2-methyl-2-propanol, CAS 75-65-0, EC 200-889-7 | HOtBu |
| Sodium hydroxide | CAS 1310-73-2, EC 215-185-5 | NaOH |
| Potassium hydroxide | CAS 1310-58-3, EC 215-181-3 | KOH |
| Methyl tert-butyl ether | tert-Butyl methyl ether, CAS 1634-04-4, EC 216-653-1 | MTBE |
| Ethyl acetate | Acetic acid ethyl ester, CAS 141-78-6, EC 205-500-4 | EA |
| Methyl ethyl ketone | Ethyl methyl ketone, 2-butanone, CAS 78-93-3, EC 201-159-0 | MEK |
| 2,6-di-tert-Butyl-4-methylphenol | 2,6-Di-tert-butyl-p-cresol, Butylated hydroxytoluene, Butylhydroxytoluene, DBPC, CAS 128-37-0, EC 204-881-4 | BHT |
| hydroquinone | 1,4-dihydroxybenzene, 1,4-benzenediol, CAS 123-31-9, EC 204-617-8 | HQ |

TABLE 1-continued

| | | |
|---|---|---|
| Hydroquinone monomethyl ether | 4-methoxyphenol, 4-Hydroxyanisole, 4-MP, HQMME, MEHQ, MQ-F, CAS 150-76-5, EC 205-769-8 | HQME |
| Methylene blue | 3,7-bis(Dimethylamino)phenazathionium chloride, Basic Blue 9, Tetramethylthionine chloride, CAS 7220-79-3, EC 200-515-2 | |
| Sodium carbonate | CAS 497-19-8, EC 207-838-8 | Na2CO3 |
| Potassium carbonate | CAS 584-08-7, EC 209-529-3 | KC2CO3 |
| Persulfate | Pentapotassium bis(peroxymonosulphate) bis(sulphate) (i.e. triple salt 2 $KHSO_5$ *•$KHSO_4$•* $K_2SO_4$), CAS 70693-62-8, EC 274-778-7 | Oxone ® |
| Sodium peroxodisulfate | CAS 7775-27-1, EC 231-892-1 | Na2S2O8 |
| Ammonium peroxodisulfate | CAS 7727-54-0, EC 231-786-5 | (NH4)2S2O8 |
| Sodium bromide | CAS 7647-15-6, EC 231-599-9 | NaBr |
| Potassium bromide | CAS 7758-02-3, EC 231-830-3 | KBr |
| Ammonium bromide | CAS 12124-97-9, EC 235-183-8 | NH4Br |
| Filler 1 | Non agglomerated silanized silica nano filler (50 nm); produced according to U.S. Pat. No. 6,899,948 B2 (filler C) | F1 |
| Filler 2 | Aggregated Zr/Si nanoclusters; produced as described in U.S. Pat. No. 6,730,156, column 25, preparatory example A; surface treated according to process as described in preparatory example B. | F2 |
| CPQ | Camphorquinone (CAS no. 10373-78-1) | Ini 1 |
| DPI-PF6 | Diphenyliodonium hexafluorophosphate (CAS no. 58109-40-3) | Ini2 |
| EDMAB | Ethyl 4-dimethylaminobenzoate (CAS no. 10287-53-3) | Ini3 |
| Triethylamine | | TEA |

General Procedure A: Synthesis of Diol Precursors (e.g. ÖR) Via Etherification of Dihydroxybenzenes (e.g. Resorcinol, Catechol or tert-Butylcatechol) with Halogenated Alcohols (e.g. 3-Chloro-1-propanol and/or 2-(2-Chloroethoxy)ethanol)

To a solution of the corresponding dihydroxybenzene and the corresponding halogenated alcohol/s in water an aqueous solution of alkaline hydroxide (e.g. NaOH) or alkaline carbonate (e.g. $Na_2CO_3$) or ammonia is added at reflux. Optionally the synthesis can be done under a protective gas atmosphere (e.g. nitrogen).

After stirring over night at reflux the reaction mixture is cooled to room temperature, and the reaction mixture is extracted (e.g. MTBE or EA or MEK) if water is used as solvent. Optionally the reaction mixture can be extracted as it is or the organic phase can be separated and only the aqueous phase can be extracted, afterwards the organic phase is combined with the extracts. Optionally the combined organic phases can be extracted with aqueous alkaline (e.g. NaOH) solutions and/or aqueous acid (e.g. $H_2SO_4$) solutions and/or water.

If IPA or tBuOH is used as solvent, the reaction mixture is first filtered to remove the precipitate, then the solvent is stripped off in vacuo, and then the residue is extracted against water as described above.

General Procedure B: In Situ Bromination of Diol Precursors (e.g. ÖR) Using a Mixture of a Persulfate Salt (e.g. KHSO5) and a Bromide Salt (e.g. NH4Br)

Following *Synthesis* 2010, 10, 1629-1632, the diol precursor (e.g. ÖR) is mono-brominated to give the corresponding mono-brominated diol precursor (e.g. BrÖR) using one equivalent of bromination reagent or dibrominated to give the corresponding Dibrominated Diol Precursor (e.g. DiBrÖR) using two equivalents of bromination reagent. This bromination reagent is a mixture of a persulfate salt (e.g. Oxone®, $Na_2S_2O_8$ or $(NH_4)_2S_2O_8$) and a bromide salt (e.g. NaBr, KBr or NH4Br). Water or methanol or a methanol/water mixture can be used as solvent.

After bromination in aqueous solution the reaction mixture is extracted (e.g. MTBE or EA or MEK). Otherwise the solvent has to be stripped off before extraction.

General Procedure C: Acid Catalyzed (e.g. MSA) Esterification of Brominated Diol Precursors (e.g. BrÖR or DiBrÖR) with Unsaturated Acids (e.g. MA)

To the corresponding Brominated Diol Precursor in e.g. cyclohexane or a hexane/toluene mixture or a cyclohexane/toluene mixture BHT, HQME, optionally methylene blue and/or HQ, the catalyst (e.g. MSA) and the unsaturated acid (e.g. MA) are added. At reflux water is removed using a Dean Starck apparatus. After completion of the reaction the crude reaction mixture is extracted at least twice with 4N NaOH solution or 2N NaOH solution, then at least once washed with water, and then dried over anhydrous $Na_2SO_4$. Then the solvent is stripped off in vacuo while air is bubbling through the crude sample.

E4R-MA (Comparative Example 1)

According to General Procedure A 51.0 g of resorcinol, 47.7 g of NaOH, and 138.5 g of 2-(2-chloroethoxy)-ethanol were reacted in 200 mL of water to give 104.1 g of E4R. According to General Procedure C 190.0 g of E4R, 12.3 g of MSA, and 171.4 g of MA were reacted to give 238.9 g of E4R-MA.

ÖR-MA (Comparative Example 2)

According to General Procedure A 51.0 g of resorcinol, 47.7 g of NaOH, 69.2 g of 2-(2-chloroethoxy)-ethanol, and 51.5 g of 3-chloro-1-propanol were reacted in 200 mL of water to give 93.5 g of ÖR. According to General Procedure C 55.0 g of ÖR, 3.80 g of MSA, and 55.4 g of MA were reacted to give 71.4 g of ÖR-MA.

DiBrE4R-MA (Inventive Example 1)

According to General Procedure A 51.0 g of resorcinol, 47.7 g of NaOH, 69.2 g of 2-(2-chloroethoxy)-ethanol, and 51.5 g of 3-chloro-1-propanol were reacted in 200 mL of water to give 93.5 g of E4R. According to General Procedure B 64.8 g of E4R, 51.0 g of NH4Br, and 181.5 g of Oxone® were reacted to give 97.4 g of DiBrE4R. According to General Procedure C 51.2 g of DiBrE4R, 3.30 g of MSA, and 27.2 g of MA were reacted to give 50.3 g of DiBrE4R-MA.

DiBrÖR-MA (Inventive Example 2)

According to General Procedure A 51.0 g of resorcinol, 47.7 g of NaOH, 69.2 g of 2-(2-chloroethoxy)-ethanol, and 51.5 g of 3-chloro-1-propanol were reacted in 200 mL of water to give 93.5 g of ÖR. According to General Procedure B 64.8 g of ÖR, 51.0 g of NH4Br, and 181.5 g of Oxone® were reacted to give 97.4 g of DiBrÖR. According to General Procedure C 51.2 g of DiBrÖR, 3.30 g of MSA, and 31.9 g of MA were reacted to give 57.9 g of DiBrÖR-MA.

Synthesis of Light Curing One Component Compositions

Some of the compounds synthesized were used for producing a (dental) composition. The compositions produced and tested with respect to their mechanical properties are given in Table 2 below. In Table 2 the values of the components represent %-weight of the individual components in the corresponding dental formulation.

General Procedure I

With magnetic stirring and under the exclusion of light the initiator system components were dissolved within the monomers at temperatures not above 50° C. (depending on the intrinsic viscosity of the used monomers).

General Procedure II

According to General Procedure I the initiator system components were dissolved within the monomers. Under the exclusion of light and using a two-arm kneader the filler was mixed in portions with this mixture of initiator system and monomers. The amount of filler was manually determined depending on the desired handling properties of the dental composition. The dental composition was then light cured using an 800 mW halogen curing light (Elipar™ Trilight; 3M Oral Care) and tested according to the corresponding measurements listed above. The respective values are given in Table 2.

Dental Compositions A and B contain either of components CE1 or CE2 but not compound (A) according to the invention. In Table 2 below, compound (A) is represented by components IE1, and IE2.

Thus, Dental Compositions A and B can be considered as Comparative Examples, whereas Dental Compositions C and D can be considered as Inventive Examples.

TABLE 2

|  | Dental Composition | | | |
|---|---|---|---|---|
|  | A | B | C | D |
| CE1 | 26.05 | | | |
| CE2 | | 26.05 | | |
| IE1 | | | 26.05 | |
| IE2 | | | | 26.05 |

TABLE 2-continued

|  | Dental Composition | | | |
|---|---|---|---|---|
|  | A | B | C | D |
| Ini1 | 0.05 | 0.05 | 0.05 | 0.05 |
| Ini2 | 0.13 | 0.13 | 0.13 | 0.13 |
| Ini3 | 0.27 | 0.27 | 0.27 | 0.27 |
| F1 | 6.98 | 6.98 | 6.98 | 6.98 |
| F2 | 66.52 | 66.52 | 66.52 | 66.52 |
| FS [MPa] | 144 ± 13.0 | 149 ± 12.0 | 148 ± 13.0 | 138 ± 11.0 |
| E-M [GPa] | 9.10 ± 0.30 | 9.4 ± 0.30 | 11.7 ± 0.40 | 12.4 ± 0.30 |

As can be seen, compositions containing the brominated polymerizable monomer described in the present text are superior with respect to E-Modulus compared to compositions containing polymerizable monomer of the prior art.

What is claimed is:

1. A dental composition comprising:

a filler matrix in an amount of at least 25 wt. % with respect to the weight of the dental composition;

an initiator system; and a resin matrix comprising a brominated polymerizable monomer(s), the brominated polymerizable monomer(s) characterized by formula (I):

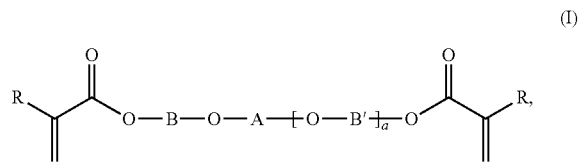

wherein:

a is an integer selected from 0 and 1,

A is selected from:

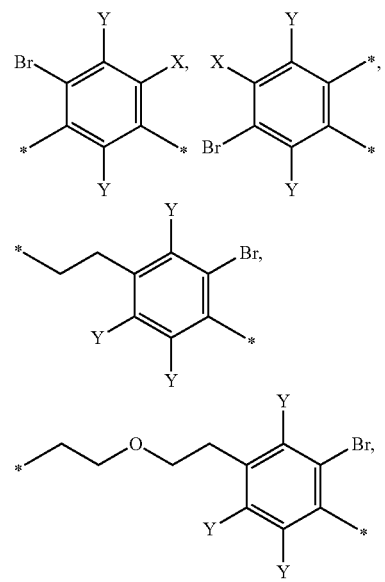

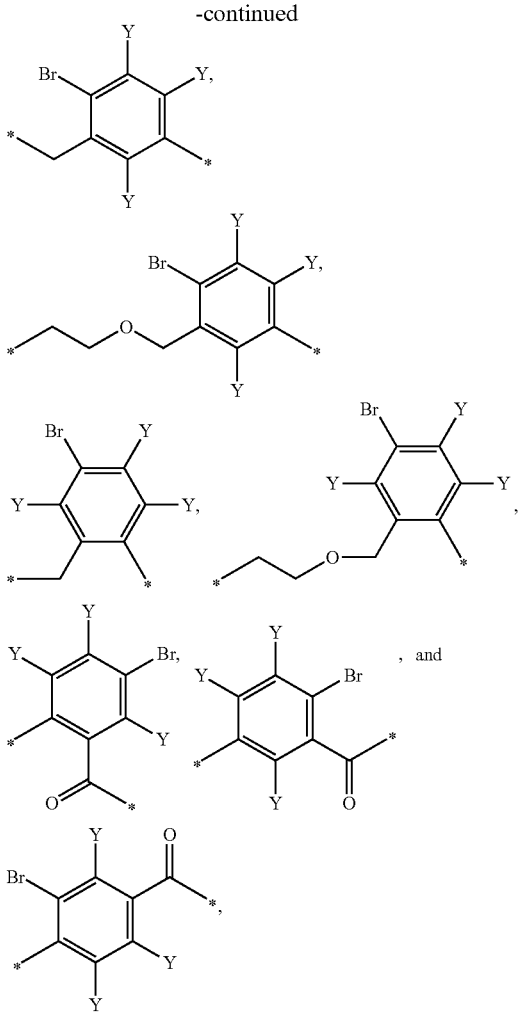

B is selected from:

*—(CH$_2$)$_b$—*, *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*,

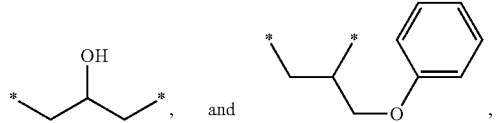

b is an integer selected from 2 to 6,

B' is selected from *—(CH$_2$)$_{b'}$—*, *—(CH$_2$—CH$_2$—O—CH$_2$—CH$_2$)—*,

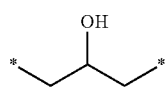

b' is an integer selected from 2 to 6,
R is H or methyl,
X is selected from H, C$_{1-6}$ alkyl, and Br,
each Y is independently H or Br,
wherein "*" represents bonding site(s).

2. The dental composition of claim 1, the brominated polymerizable monomer(s) being characterized by:
having a molecular weight of 400 to 800 g/mol;
not solidifying at 23° C.;
viscosity: 0.2 to 3 Pa*s at 23° C.;
having a refractive index in the range of 1.52 to 1.56; or
a combination thereof.

3. The dental composition of claim 1, the brominated polymerizable monomer(s) being selected from:

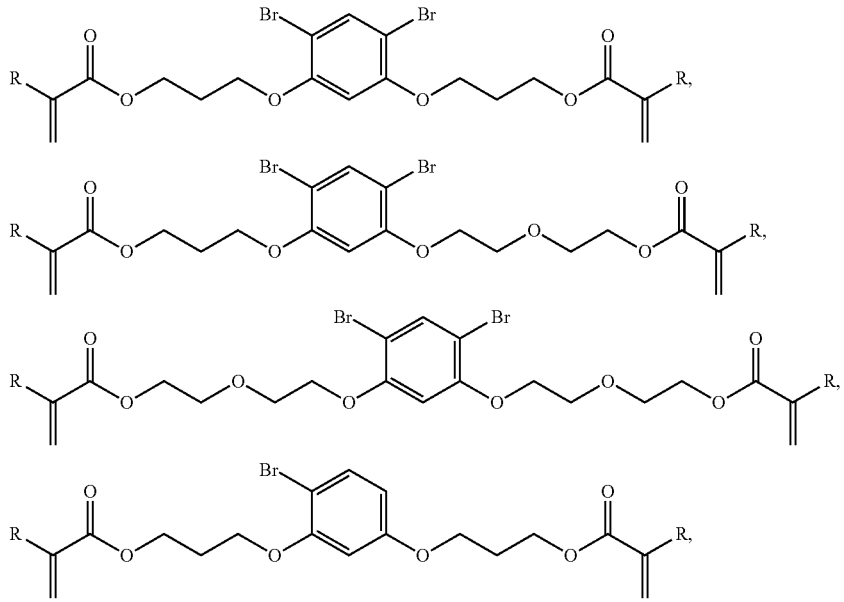

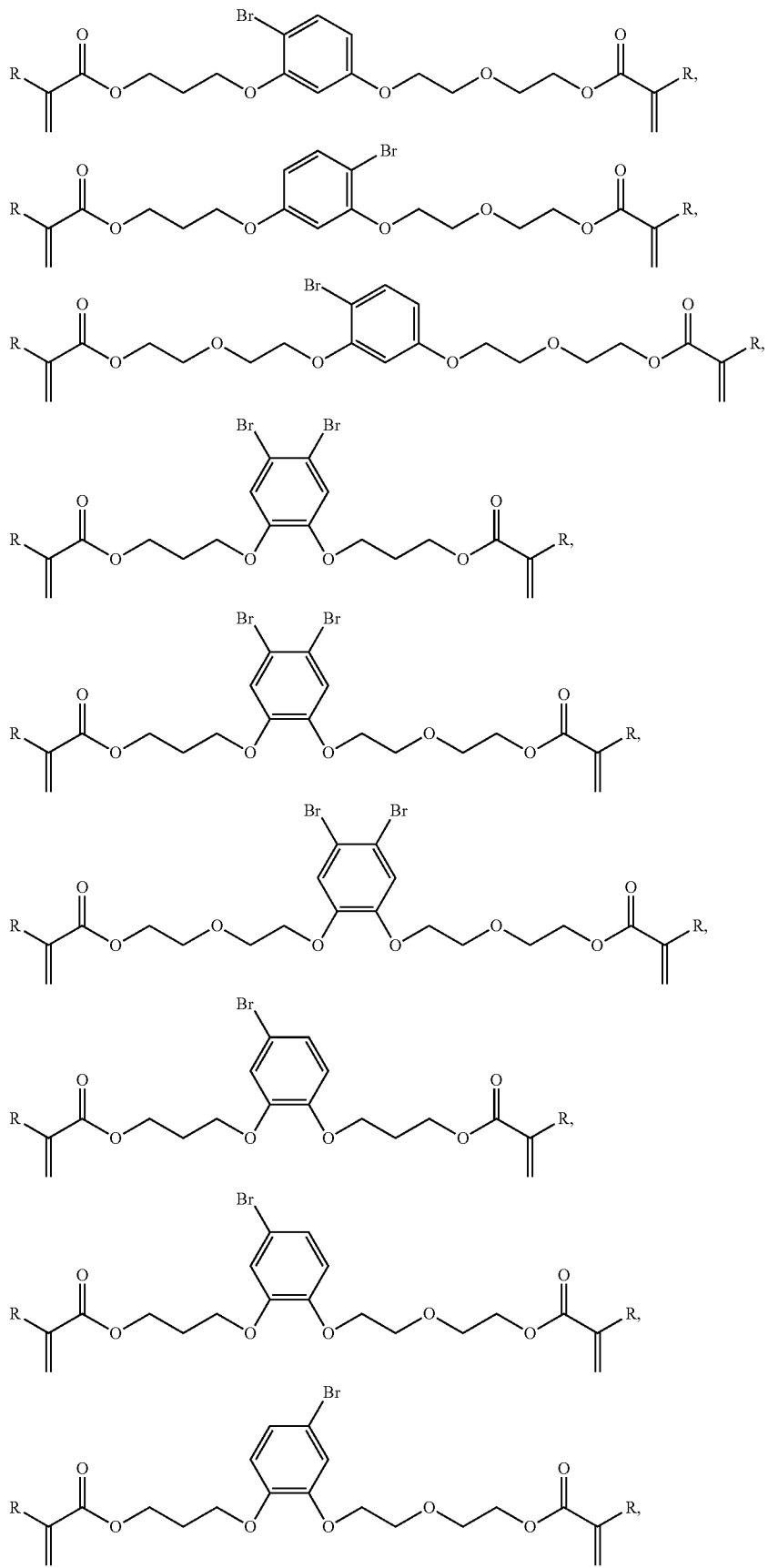

-continued

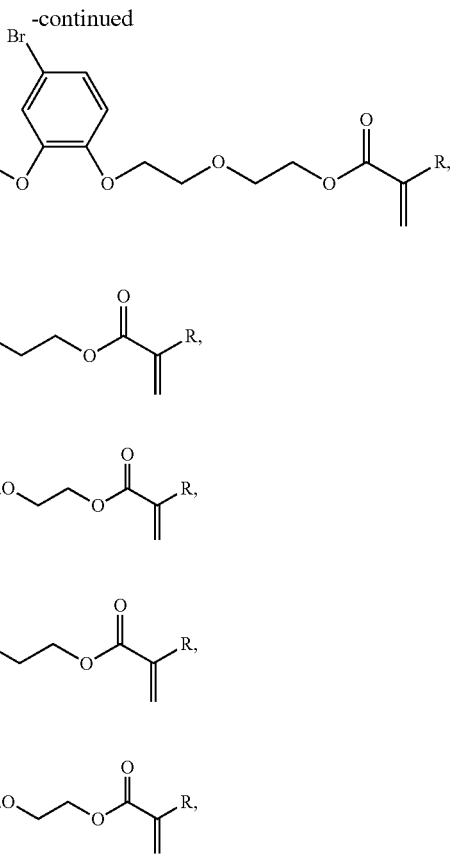

and a combination thereof, each R is independently selected from H and CH$_3$.

4. The dental composition of claim 1, the initiator system comprising radiation curing initiators, redox-curing initiators, heat-curing initiators, or a combination thereof.

5. The dental composition of claim 1, the filler system comprising:
aggregated nano filler(s),
agglomerated nano filler(s),
discrete nano filler(s),
or a combination thereof.

6. The dental composition of claim 1, comprising the components in the following amounts:
resin matrix: 5 to 70 wt. %,
filler matrix: 25 to 90 wt. %, and
initiator system: 0.1 to 10 wt. %,
wherein wt. % is with respect to the weight of the dental composition.

7. The dental composition of claim 1, further comprising:
non-brominated, non-acidic polymerizable monomer(s) present in an amount of 1 to 50 wt. %;
non-brominated, acidic polymerizable monomer(s) present in an amount of 1 to 50 wt. %;
additive(s) present in an amount of 0.1 to 5 wt. %; or
a combination thereof.

8. The dental composition of claim 1, being characterized by the following prior to hardening:
viscosity: 5 to 200 Pa*s measured at 23° C.;
pH value: 2 to 8, if brought in contact with wet pH-sensitive paper;
being storage stable for at least 3 months; or
a combination thereof.

9. The dental composition claim 1, being characterized by the following after hardening:
flexural strength: at least 100 MPa according to ISO 4049:2009(E);
E-modulus: at least 10 MPa according to ISO 4049:2009 (E);
shape: dental crown, bridge, inlay, onlay or veneer; or
a combination thereof.

10. The dental composition of claim 1, comprising:
water or C$_1$ to C$_4$ alcohols in an amount of no more than 10 wt. %;
bisphenol A-glycidyl methacrylate in an amount of no more than 10 wt. %; or
a combination thereof,
wherein wt. % is with respect to the whole composition.

11. The dental composition of claim 1,
the initiator system comprising a radiation curing initiator, a redox-curing initiator, or a combination thereof, and
the filler matrix present in an amount of 25 to 90 wt. %, the filler matrix comprising nano-fillers selected from aggregated nano filler(s), agglomerated nano filler(s), discrete nano filler(s), and a combination thereof, wherein:

A is selected from:

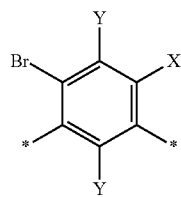 and 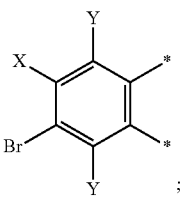 ;

B is independently selected from:
*—(CH$_2$)$_b$—*, *—(CH$_2$—CH$_2$—O—CH$_2$—CH$_2$)—*, *—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)—*, and

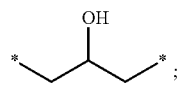 [SMILES: *CC(O)C*] ;

and

X is selected from H, methyl, ethyl, hexyl, tert-butyl, and Br, and wherein the resin matrix is present in an around from 5 to 75 wt. %.

12. The dental composition of claim 1, for use in producing a dental restorative material.

13. A kit of parts comprising:
the dental composition of claim 1 in a hardened or unhardened state;
one or more of:
a dental adhesive,
a dental cement, and
an applicator; and
a set of instructions directing a user to contact the dental composition to a tooth surface.

14. A dental milling block comprising the dental composition of claim 1 in its hardened state.

* * * * *

UNITED STATES PATENT AND TRADEMARK OFFICE
CERTIFICATE OF CORRECTION

| | | |
|---|---|---|
| PATENT NO. | : 10,932,995 B2 | |
| APPLICATION NO. | : 16/762170 | |
| DATED | : March 2, 2021 | |
| INVENTOR(S) | : Adrian Eckert | |

It is certified that error appears in the above-identified patent and that said Letters Patent is hereby corrected as shown below:

In the Claims

Column 54,
Line 5, Claim 11, delete "around" and insert -- amount --, therefor.

Signed and Sealed this
Tenth Day of January, 2023

Katherine Kelly Vidal
*Director of the United States Patent and Trademark Office*